US012344667B2

(12) United States Patent
Nanchahal et al.

(10) Patent No.: US 12,344,667 B2
(45) Date of Patent: Jul. 1, 2025

(54) METHOD OF TREATING EARLY STAGE DUPUYTREN'S DISEASE

(71) Applicant: 180 Therapeutics LP, Cambridge, MA (US)

(72) Inventors: Jagdeep Nanchahal, Oxford (GB); Glenn R. Larsen, Sudbury, MA (US); Marc Feldmann, London (GB)

(73) Assignee: 180 THERAPEUTICS LP, Cambridge, MA (US)

( * ) Notice: Subject to any disclaimer, the term of this patent is extended or adjusted under 35 U.S.C. 154(b) by 0 days.

(21) Appl. No.: 16/089,234

(22) PCT Filed: Apr. 6, 2017

(86) PCT No.: PCT/US2017/026382
§ 371 (c)(1),
(2) Date: Sep. 27, 2018

(87) PCT Pub. No.: WO2017/177021
PCT Pub. Date: Oct. 12, 2017

(65) Prior Publication Data
US 2021/0040196 A1    Feb. 11, 2021

Related U.S. Application Data

(60) Provisional application No. 62/459,321, filed on Feb. 15, 2017, provisional application No. 62/424,909, filed on Nov. 21, 2016, provisional application No. 62/397,728, filed on Sep. 21, 2016, provisional application No. 62/367,500, filed on Jul. 27, 2016, provisional application No. 62/320,151, filed on Apr. 8, 2016.

(51) Int. Cl.
*A61K 39/395* (2006.01)
*C07K 16/24* (2006.01)
*A61K 39/00* (2006.01)

(52) U.S. Cl.
CPC ...... *C07K 16/241* (2013.01); *A61K 2039/505* (2013.01)

(58) Field of Classification Search
None
See application file for complete search history.

(56) References Cited

U.S. PATENT DOCUMENTS

2009/0291062 A1*  11/2009  Fraunhofer .............. A61K 9/08
                                          424/85.5
2012/0232031 A1    9/2012  Hutchinson et al.
2013/0287760 A1*  10/2013  Nanchahal ............ A61K 9/0019
                                          424/94.67

FOREIGN PATENT DOCUMENTS

WO   WO 2012/056044 A1   5/2012
WO   WO 2015/006469 A2   1/2015

OTHER PUBLICATIONS

Laursen et al, Basic and Clinical Pharmacology and Toxicologym 2006, vol. 98, p. 218-221.*
PCT International Application Publication No. WO 2012/056044 A1, published May 3, 2012 to Nanchahal et al. (Exhibit 1).
Reed, et al., "Local Anesthesia Part 2: Technical Considerations", Anesthesia Progress, May 28, 2012, vol. 59, No. 3, pp. 127-137 (Exhibit 2).
International Search Report issued in connection with PCT International Application No. PCT/US2017/026382 (Exhibit 3).
Written Opinion of the International Searching Authority issued in connection with PCT International Application No. PCT/US2017/026382 (Exhibit 4).
Reed, et al., "Local Anesthesia Part . 2: Technical Considerations", Anesthesia Progress, May 28, 2012, vol. 59, No. 3, pp. 127-137.
International Search Report issued in connection with PCT International Application No. PCT/US2017/026382.
Written Opinion of the International Searching Authority issued in connection with PCT International Application No. PCT/US2017/026382.
Getting to Know Humira (adalimumab) Citrate-free, Humira injection package insert summary—https: //www.humira.com/citrate-free.
Verjee, Liaquat S. et al. "Unraveling the signaling pathways promoting fibrosis in Dupuytren's disease reveals TNF as a therapeutic target" Proceedings of the National Academy of Sciences (PNAS), vol. 110, No. 10, (Feb. 19, 2013): E928-E937.
Nanchahal, Jagdeep et al. "Anti-tumour necrosis factor therapy for Dupuytren's disease: a randomised dose response proof of concept phase 2a clinical trial" EBioMedicine vol. 33 (Jul. 6, 2018): pp. 282-288.
Satish, Latha, "Cytokine targeted therapy for Dupuytren's disease" EBioMedicine, vol. 34 (Jul. 18, 2018): pp. 14-15.

(Continued)

*Primary Examiner* — Yunsoo Kim
(74) *Attorney, Agent, or Firm* — John P. White

(57)  ABSTRACT

The subject invention provides a method of treating an individual afflicted with early stage Dupuytren's disease characterized by the presence of one or more nodules on the individual's hand which comprises injecting into each nodule a pharmaceutical composition comprising an amount of an antihuman TNFa antibody or fragment thereof effective to treat the individual, wherein the pharmaceutical composition is in the form of a liquid and between 0.1 ml and 0.6 ml of the composition is injected into each nodule. This invention also provides for a pre-filled syringe for carrying out the above-described method.

2 Claims, 18 Drawing Sheets

(56) References Cited

OTHER PUBLICATIONS

Kalliolias, George D. et al. "TNF biology, pathogenic mechanisms and emerging therapeutic strategies", Nature Reviews Rheumatology, vol. 12, No. 1, (Dec. 10, 2015), pp. 49-62.
Revicki, Dennis et al. "Adalimumab Reduces Pain, Fatigue, and Stiffness in Patients with Ankylosing Spondylitis: Results from the Adalimumab Trial Evaluating Long-Term Safety and Efficacy for Ankylosing Spondylitis (ATLAS)", The Journal of Rheumatology, vol. 35, No. 7, (Jul. 1, 2008), pp. 1346-1353.
Mar. 24, 2023 Canadian Office Action issued in connection with Canadian Patent Application No. 3,020,327.
May 11, 2023 Communication Pursuant to Article 94(3) EPC issued in connection with European Patent Application No. 17779836.0-1111.
Jun. 1, 2023 Australian Office Action issued in connection with Australian Patent Application No. 2017248273.
Jun. 9, 2023 Extended European Search Report issued in connection with European Patent Application No. 23160006.5-1111.
Dec. 14, 2023 Communication pursuant to Article 94(3) EPC issued in connection with European Patent Application No. 23160006.5-1111.

* cited by examiner

Placebo 40 mg adalimumab

METHOD OF TREATING EARLY STAGE DUPUYTREN'S DISEASE

This application claims priority of U.S. Provisional Application No. 62/459,321, filed Feb. 15, 2017, U.S. Provisional Application No. 62/424,909, filed Nov. 21, 2016, U.S. Provisional Application 62/397,728, filed Sep. 21, 2016, U.S. Provisional Application 62/367,500, filed Jul. 27, 2016, and U.S. Provisional Application No. 62/320,151, filed Apr. 8, 2016, the contents of each of which are hereby incorporated by reference in their entirety.

Throughout this application, various publications are referred by first author and year of publication. Full citations for these publications are presented in a section entitled References immediately preceding the claims. The disclosures of these publications in their entireties are hereby incorporated by reference into this application in order to more fully describe the state of the art to which the invention relates.

BACKGROUND OF INVENTION

Dupuytren's disease also known as palmar fibromatosis (or in its established disease state Dupuytren's contracture) is a disease associated with the buildup of extracellular matrix materials such as collagen on the connective tissue of the hand (the palmar fascia) causing it to thicken and shorten with the result that the fingers curl into the palm.

Dupuytren's disease is a common fibrotic disorder (Hindocha, 2009). The mean age of treatment for the disease is 63 years (Chen, 2011). It exhibits a strong hereditary basis (Hurst, 2009). Dupuytren's disease causes the fingers to curl irreversibly into the palm, leading to significant impairment of hand function.

There is no approved treatment for early disease. In fact, a recent systematic review has highlighted the lack of efficacy of all therapeutic modalities that have been tried to date, including intralesional steroid injection or radiotherapy (Ball, 2016). Once patients have established deformities, the mainstay of treatment is surgical excision (fasciectomy) of the diseased tissue or cords (Davis, 2013; Zhao, 2016). However, surgery is associated with long post operative rehabilitation and recovery and is not cost effective (Chen 2011). Surgery is recommended when patients develop flexion deformities of the digits of 30 degrees or more of the finger joints and suffer impaired hand function (Rayan, 2007). Between 10-12% of patients develop recurrence over 3 years following surgery (Ullah, 2009; van Rijssen, 2012) and are treated with more extensive surgery that involves excision of the diseased tissue and the overlying skin (dermofasciectomy). Post-operatively, patients require 3-6 months of hand therapy and splintage (Hughes, 2003; Larson, 2008). Complications occur in about 20% of surgical patients (Bulstrode, 2005) (Crean, 2011).

Alternative, less invasive techniques have been developed to disrupt the cords of diseased tissue with either a needle (Beaudreuil, 2012) or collagenase digestion (Hurst, 2009). However, recurrence rates are high, affecting 70% of patients treated with percutaneous needle fasciotomy (van Rijssen, 2012) and 35% of those treated with collagenase (Peimer 2013) at 3 years. The complication rate is 20% following needle fasciotomy (Crean, 2011) and over 70% after collagenase injection (Hurst, 2009).

In the USA and United Kingdom, a majority of patients with established disease and finger contractures are treated surgically (Davis, 2013). Over 90% of the 12,900 patients who have surgery for Dupuytren's disease per annum in the United Kingdom undergo fasciectomy. Recurrence rates are of the order of 12% within 3 years of fasciectomy and the costs for dermofasciectomy for recurrent disease are much higher (Ullah, 2009). Neither surgical fasciectomy or collagenase injection or collagenase injection was found to be an effective use of health care resources (Chen, 2011).

Intralesional steroid injection and radiotherapy are two possible treatments for early Dupuytren's disease. Intralesional steroid injection has been proposed based on a retrospective, uncontrolled and unblinded study of 63 patients with early Dupuytren's disease treated with steroid injection into the nodules at 6 week intervals (Ketchum, 2000). However, this treatment has found limited acceptance. Radiotherapy has also been used and there is no clear evidence for efficacy (Ball 2016). Moreover, 20-30% of patients developed long term adverse effects, including dry skin, increased desquamation, skin atrophy, telangiectasia, erythema, altered heat and pain sensation (Seegenschmiedt, 2001; Pohl, 2002; Betz, 2010). Based on the published data The National Institute for Health and Care Excellence (NICE) does not recommend radiotherapy for Dupuytren's disease (IPG537, 2016).

Therefore, there is a need to develop an effective therapy to prevent progression of early Dupuytren's disease while avoiding the necessity for invasive procedures. Also, there is a need to prevent the development of recurrent disease following surgery, needle fasciotomy or collagenase injection in patients with established finger contractures.

BRIEF SUMMARY OF THE INVENTION

The subject invention provides a method of treating an individual afflicted with early stage Dupuytren's disease characterized by the presence of one or more nodules on the individual's hand which comprises injecting into each nodule a pharmaceutical composition comprising an amount of an anti-human TNF antibody or fragment, thereof effective to treat the individual, wherein the pharmaceutical composition is in the form of a liquid and between 0.1 ml and 0.6 ml of the composition is injected into each nodule.

The subject invention also provides a pre-filled syringe which comprises:
a) a pharmaceutical composition in the form of a liquid comprising in a volume between 0.1 ml and 1.0 ml, an amount of an anti-human TNF antibody or fragment thereof effective to treat an individual afflicted with early stage Dupuytren's disease characterized by the presence of one or more nodules on the individual's hand and
b) a fine needle on the syringe, the size of which is equal to or greater than 25 gauge.

The subject invention also provides a method of treating an individual afflicted with early stage Dupuytren's disease characterized by the presence of one or more nodules on the individual's hand which comprises injecting into each nodule a pharmaceutical composition comprising an amount of a soluble TNF receptor effective to treat the individual, wherein the pharmaceutical composition is in the form of a liquid and between 0.1 ml and 0.6 ml of the composition is injected into each nodule.

(i) Dupuytren's cord
(ii) Dupuytren's nodule
(iii) Flexor tendon
(iv) Proximal phalanx
(v) joint
(vi) metacarpal (B) Power Doppler image of the same area. Arrow indicates hypervascular area in Dupuytren's nodule. Dotted arrow indicates digital artery.

Figure 2:
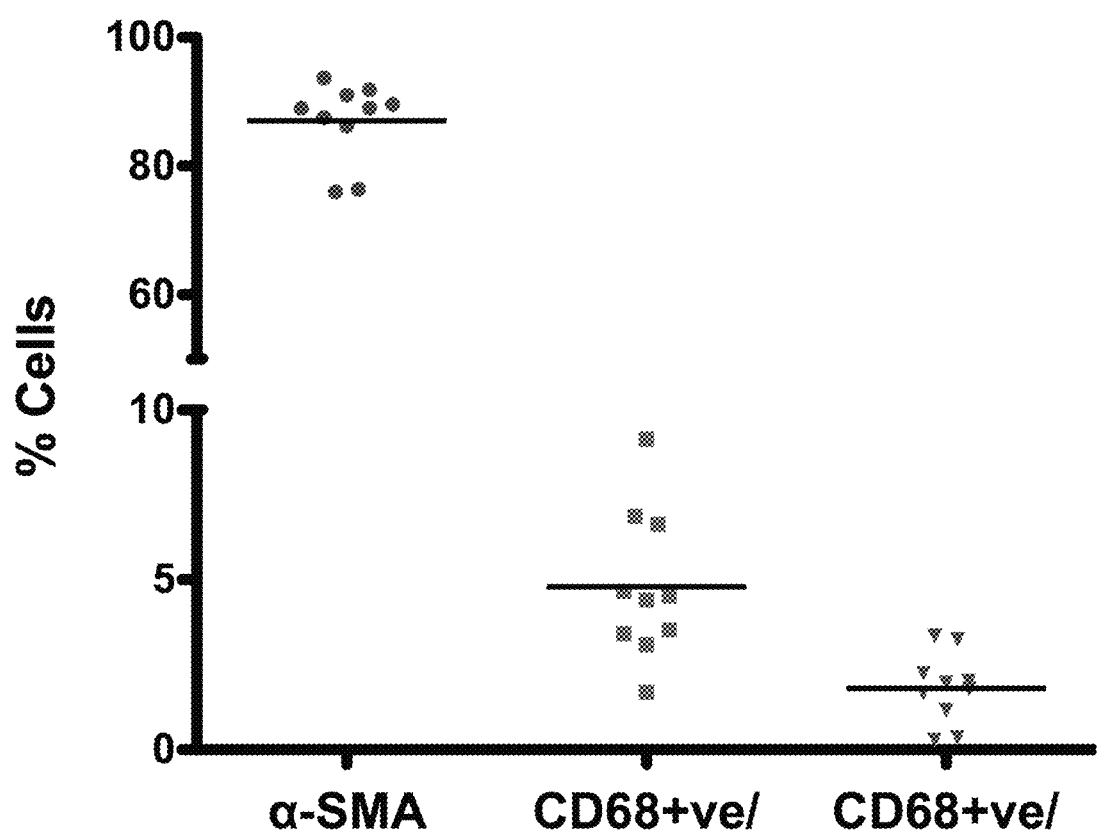

FIG. 2: Flow cytometric analysis of cells isolated from freshly disaggregated Dupuytren's nodular tissue. Intracellular α-SMA-positive (myofibroblasts; mean±SD: 87±6.1%), cell surface CD68-positive CD163-negative (classically activated M1 macrophages; mean±SD: 4.8±2.2%), and CD68-positive CD163-positive (alternatively activated M2 macrophages; mean±SD: 1.8±1.0%) cells were quantified.

Figure 3:
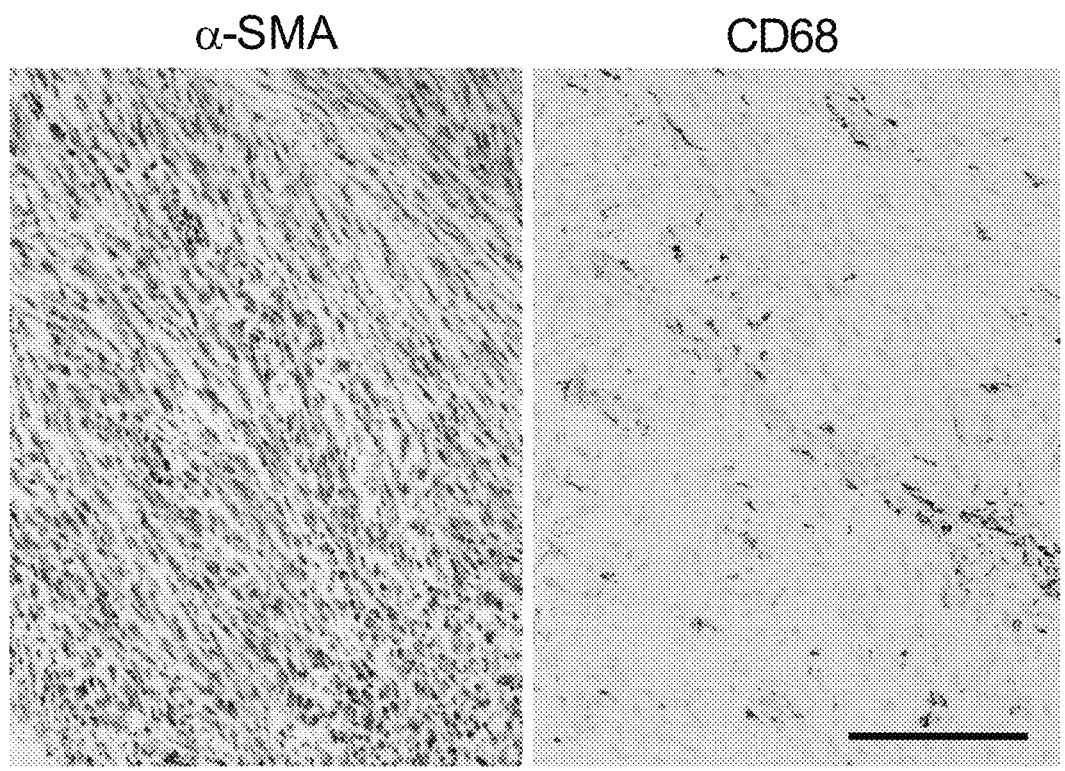

FIG. 3: Serial histological sections of Dupuytren's nodular tissue stained for α-SMA+ (myofibroblasts) and CD68+ (monocytes) cells. (Scale bar 100 μm)

Figure 4:
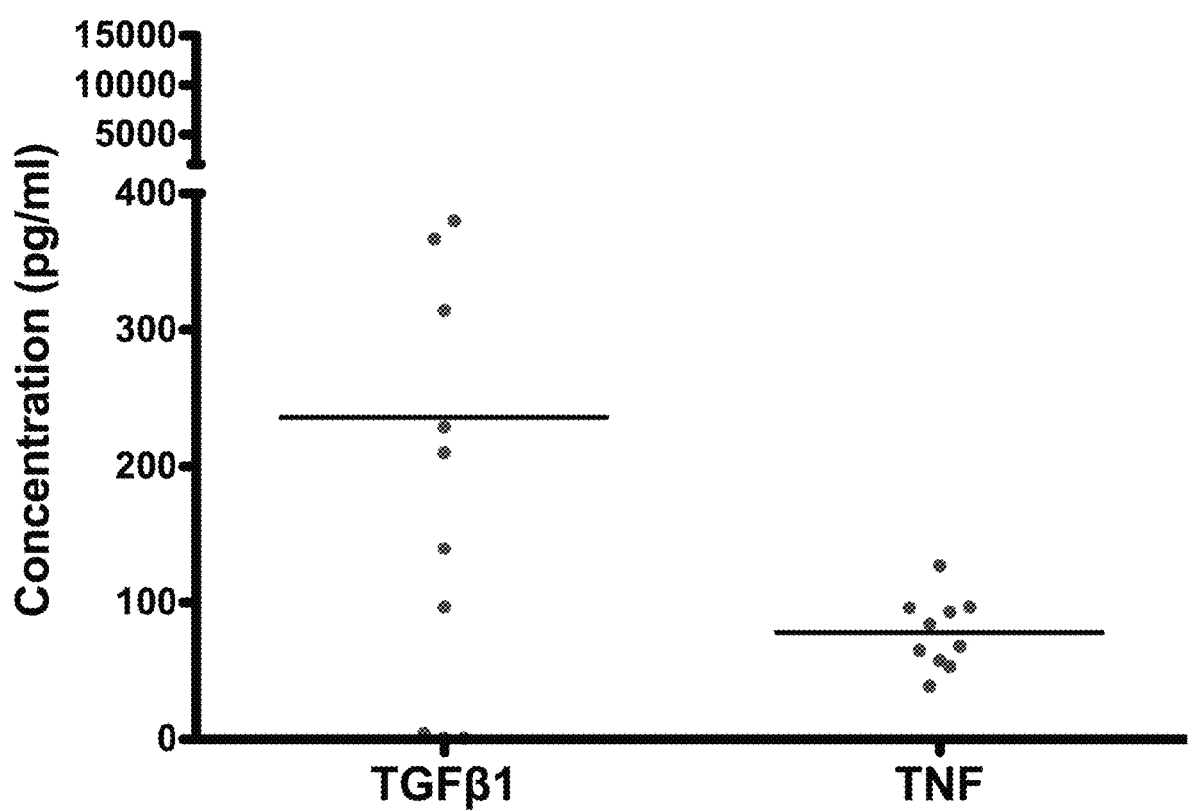

FIG. 4: Cytokines released by freshly isolated nodular cells in monolayer culture using electrochemiluminescence. All data shown are from >10 patient samples.

Figure 5:
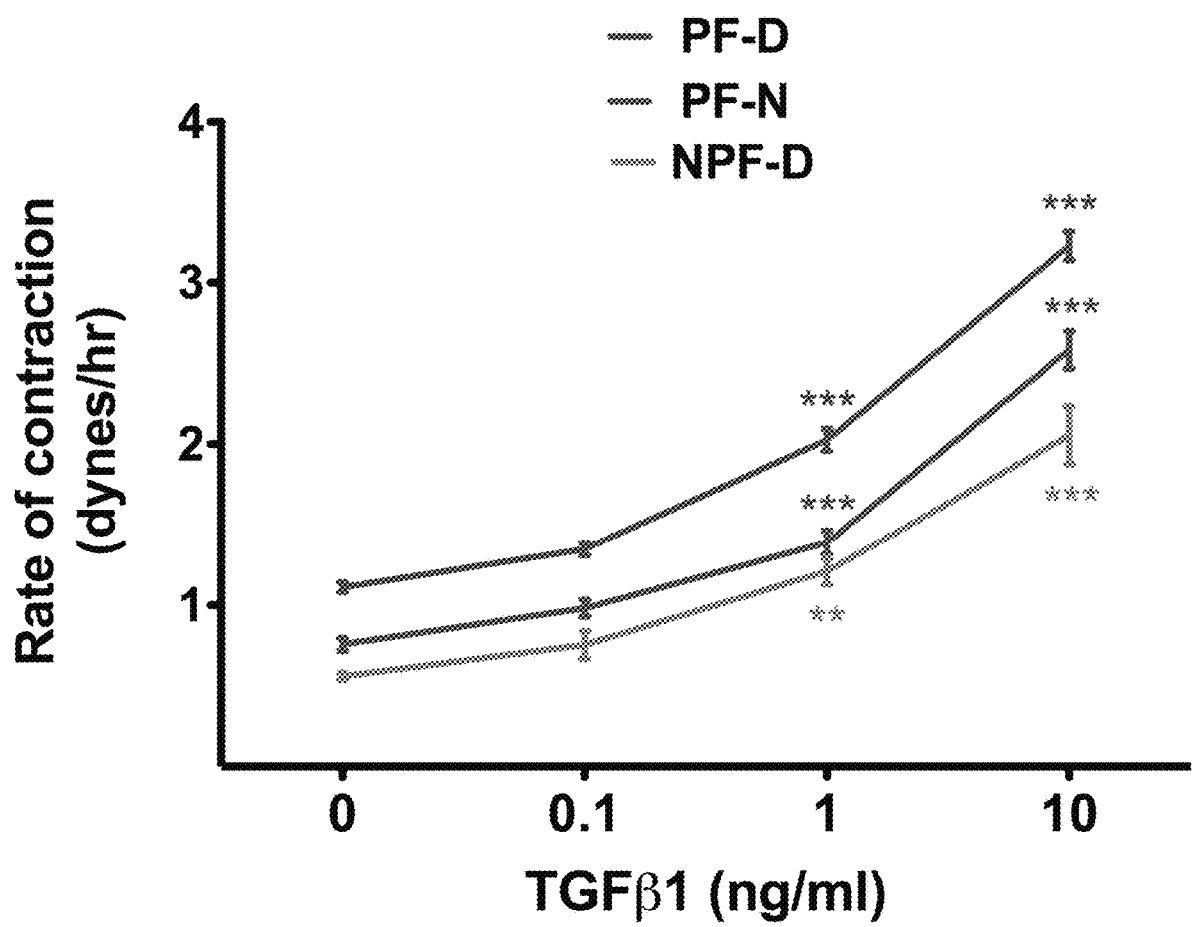

FIG. 5: TGF-β1 led to increased contractility of all three types of fibroblasts.

Figure 6:
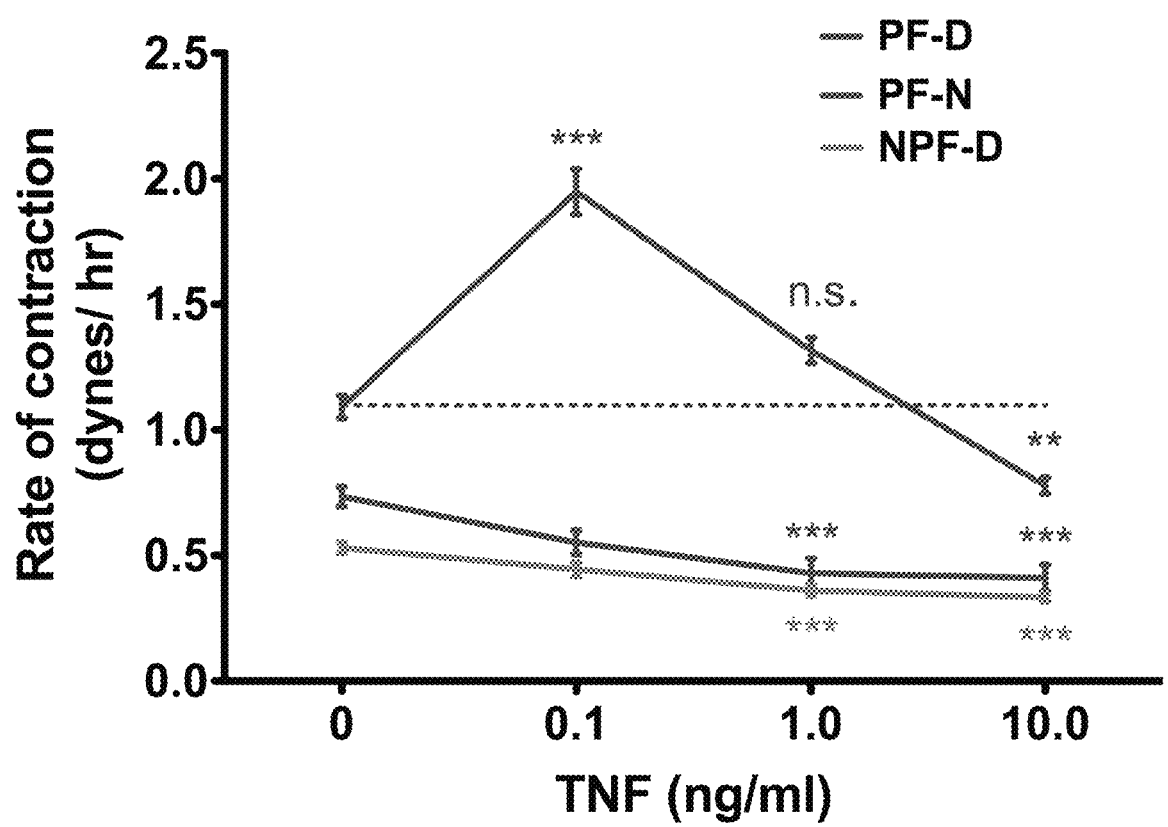

FIG. 6: Contraction of PF-D peaked on addition of 0.1 ng/mL tumour necrosis factor (TNF). In contrast, TNF treatment PF-N and NPF-D led to a dose-dependent decrease in contractility.

Figure 7:
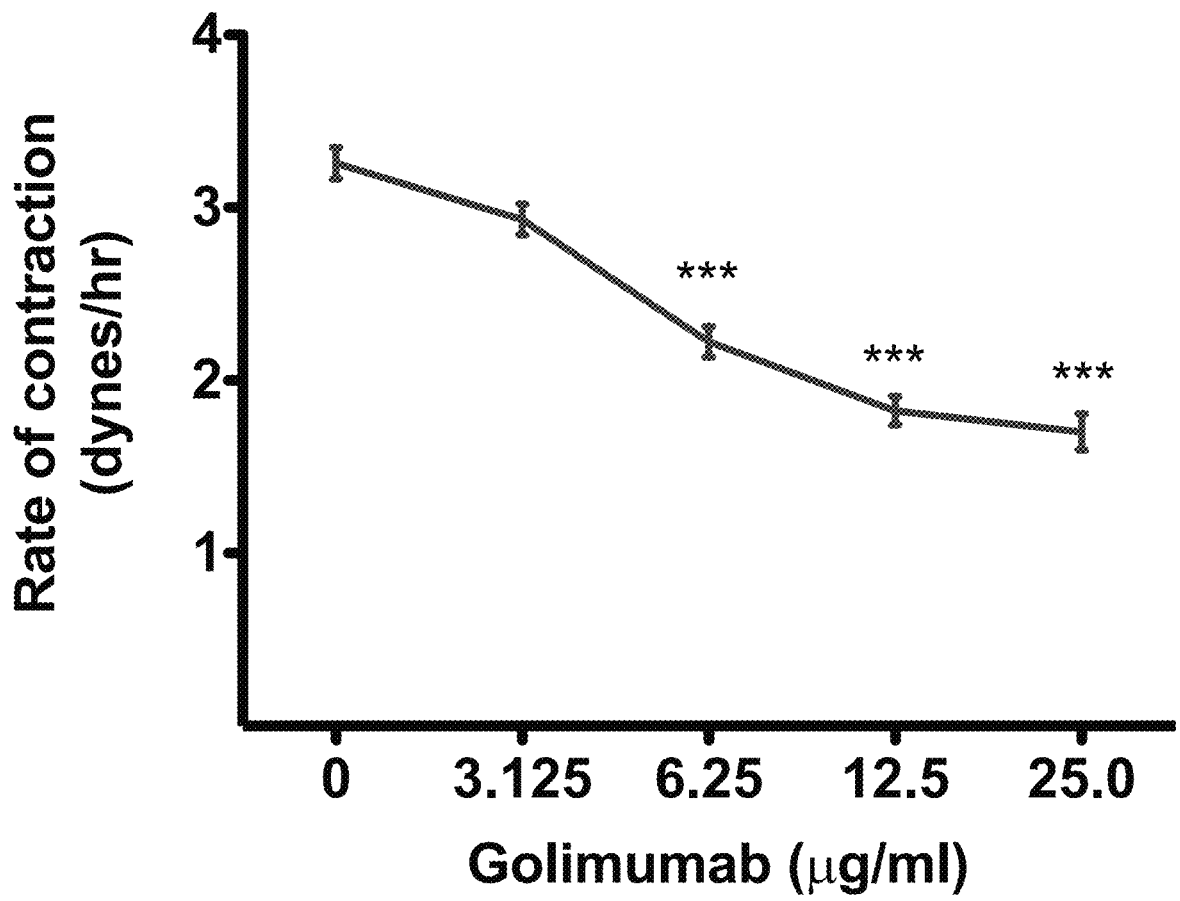

FIG. 7: Dose-response of Dupuytren's myofibroblast contraction to golimumab, an anti-TNF agent.

Figure 8:
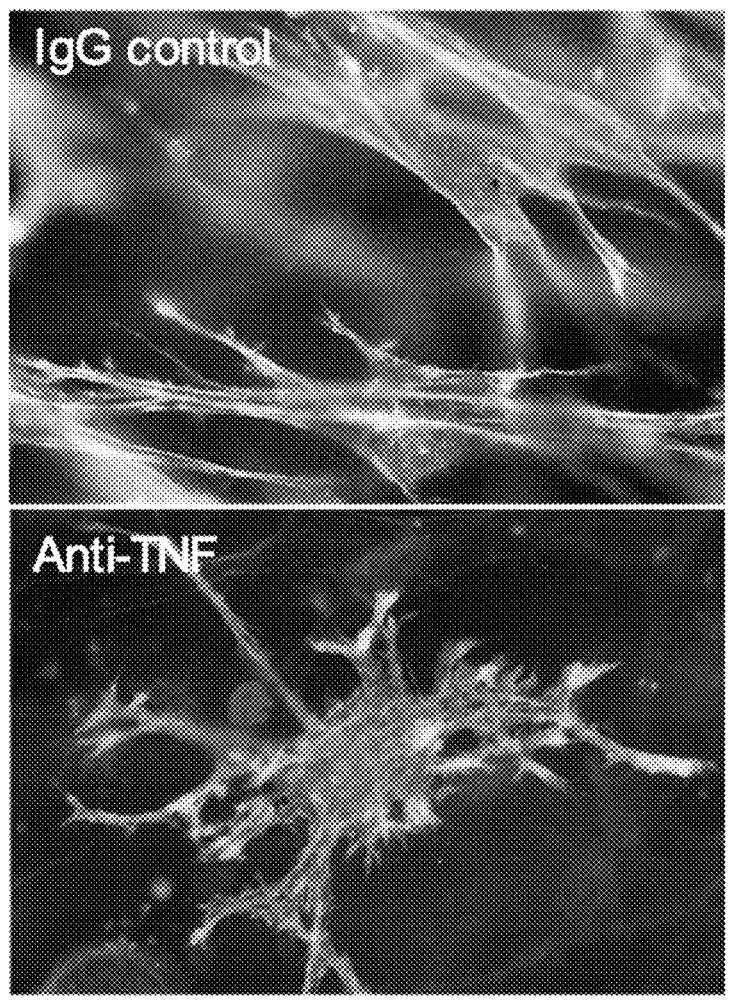

FIG. 8: immunofluoresence staining of Dupuytren's myofibroblasts seeded in 3D collagen matrices. Treatment with anti-TNF resulted in disassembly of the α-SMA fibers.

Figure 9:
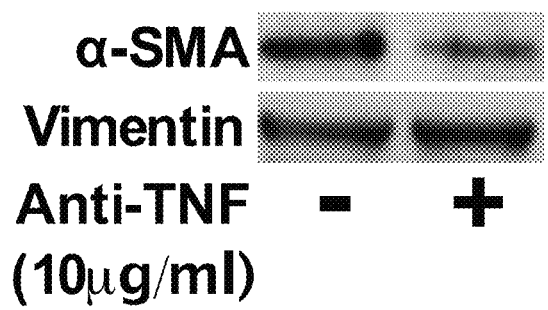

FIG. 9: TNF inhibition led to reduction of α-SMA protein expression by Dupuytren's myofibroblasts.

Figure 10:
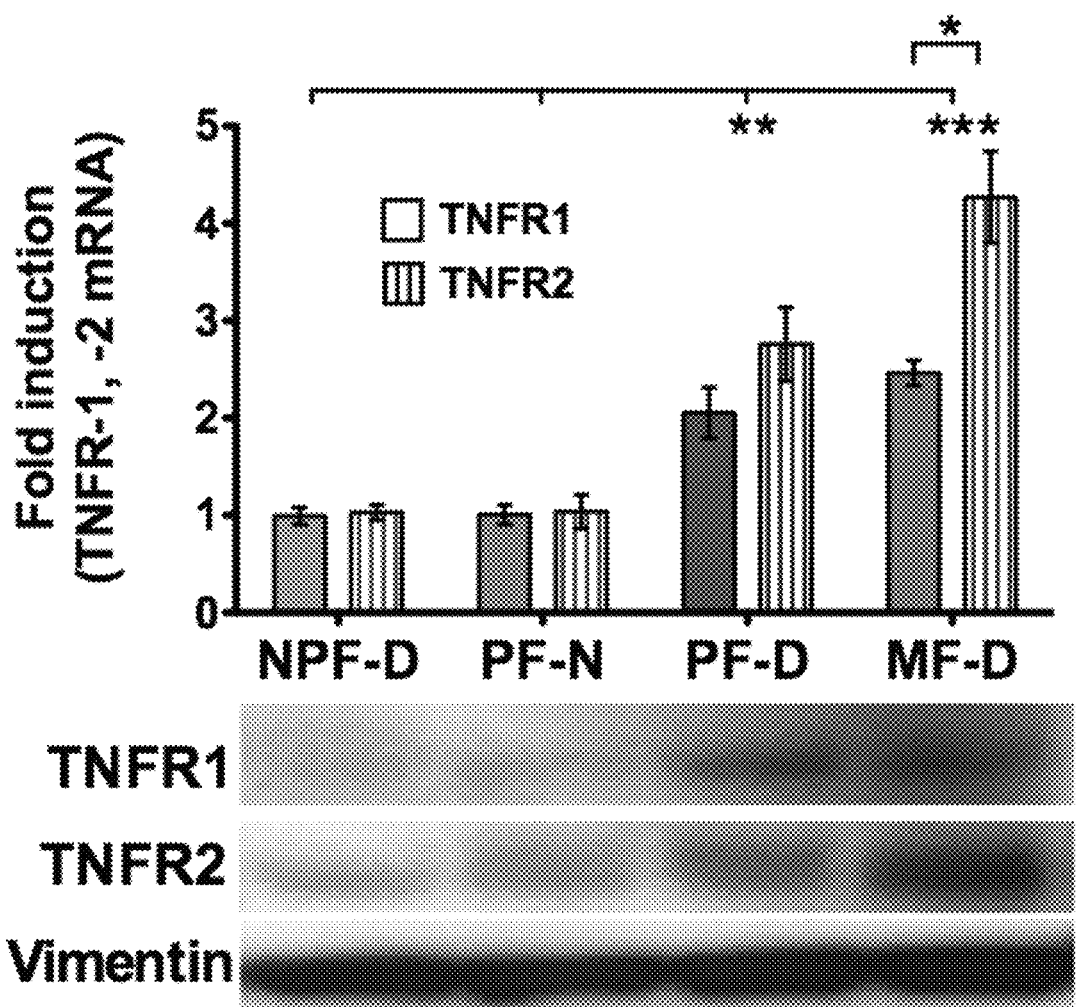

FIG. 10: Baseline gene expression of TNFR1 and TNFR2 was significantly higher in myofibroblasts and PF-D compared with both PF-N and NTF-D. In Dupuytren's myofibroblasts (MF-D), TNFR2 expression was significantly greater than TNFR1. Fold change was normalised to the baseline expression of NPF-D.

Figure 11:
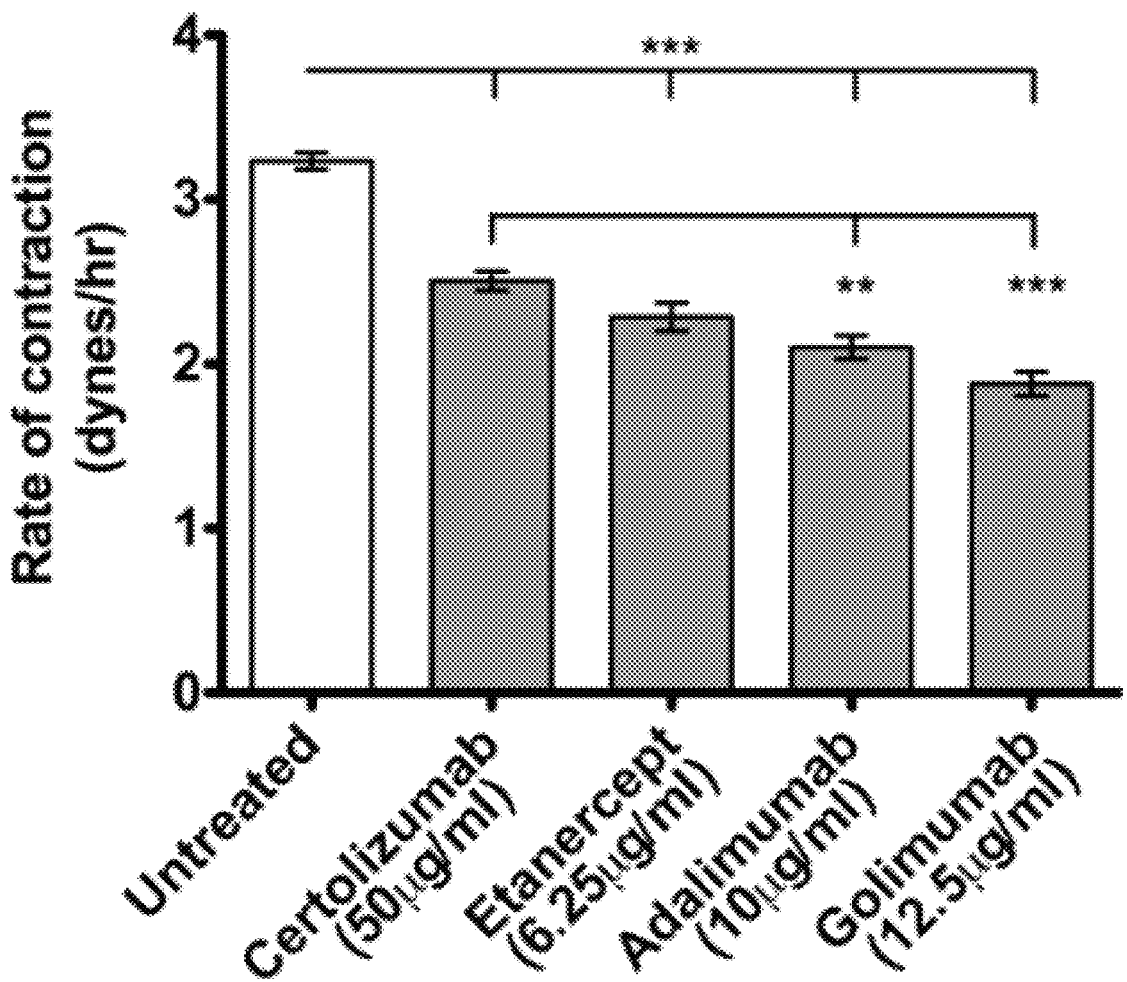

FIG. 11: Comparison of current anti-TNF preparations approved by FDA for subcutaneous administration on the contractility of Dupuytren's myofibroblasts. Doses calculated based on 25% of recommended dose in rheumatoid arthritis (certolizumab 200 mg in 1 mL every 2 wk, etanercept 50 mg in 1 mL every week, adalimumab 40 mg in 0.8 mL every 2 wk, golimumab 50 mg in 0.5 mL every 4 wk).

Figure 12:
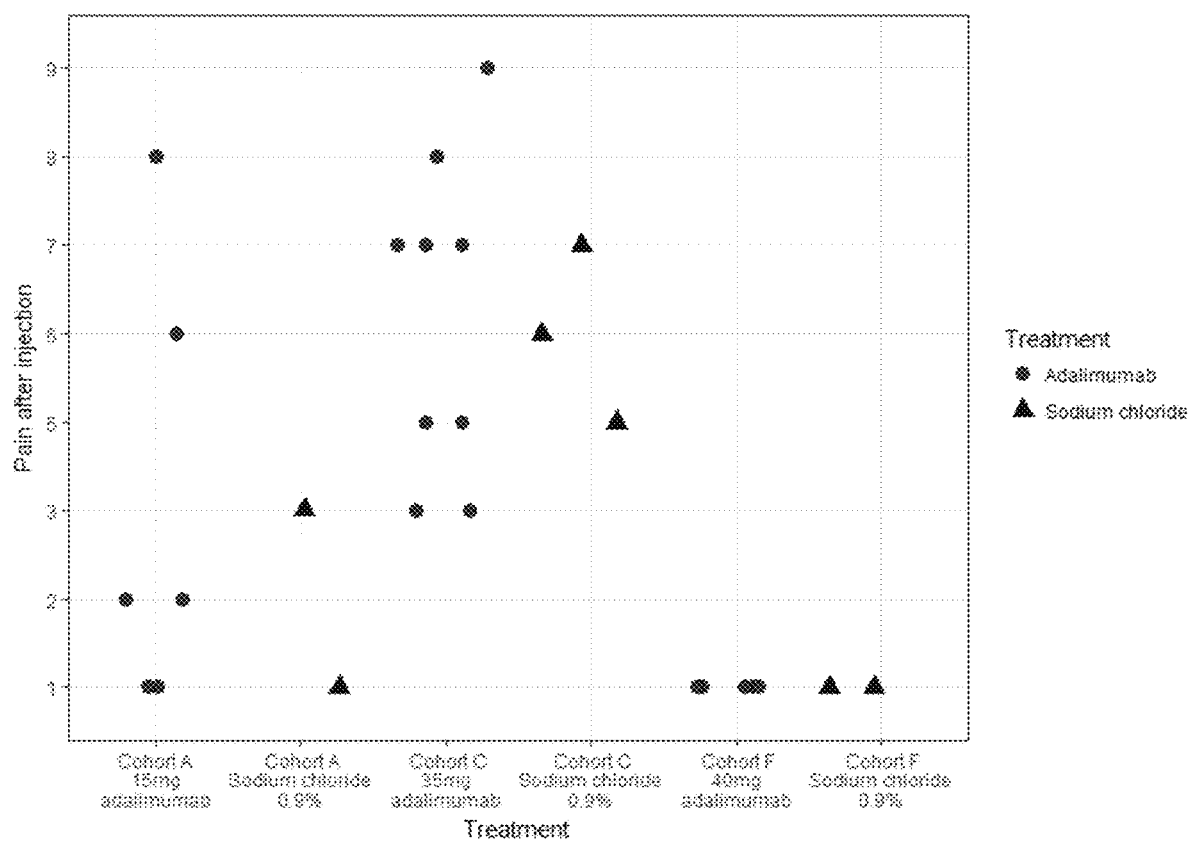

FIG. 12: Pain Scores: Scatterplot of pain, for each patient after injection. Triangle indicates treatment with abalimumab, whilst the circle indicates treatment with placebo. 1=no pain, 10=maximal pain.

Figure 13:
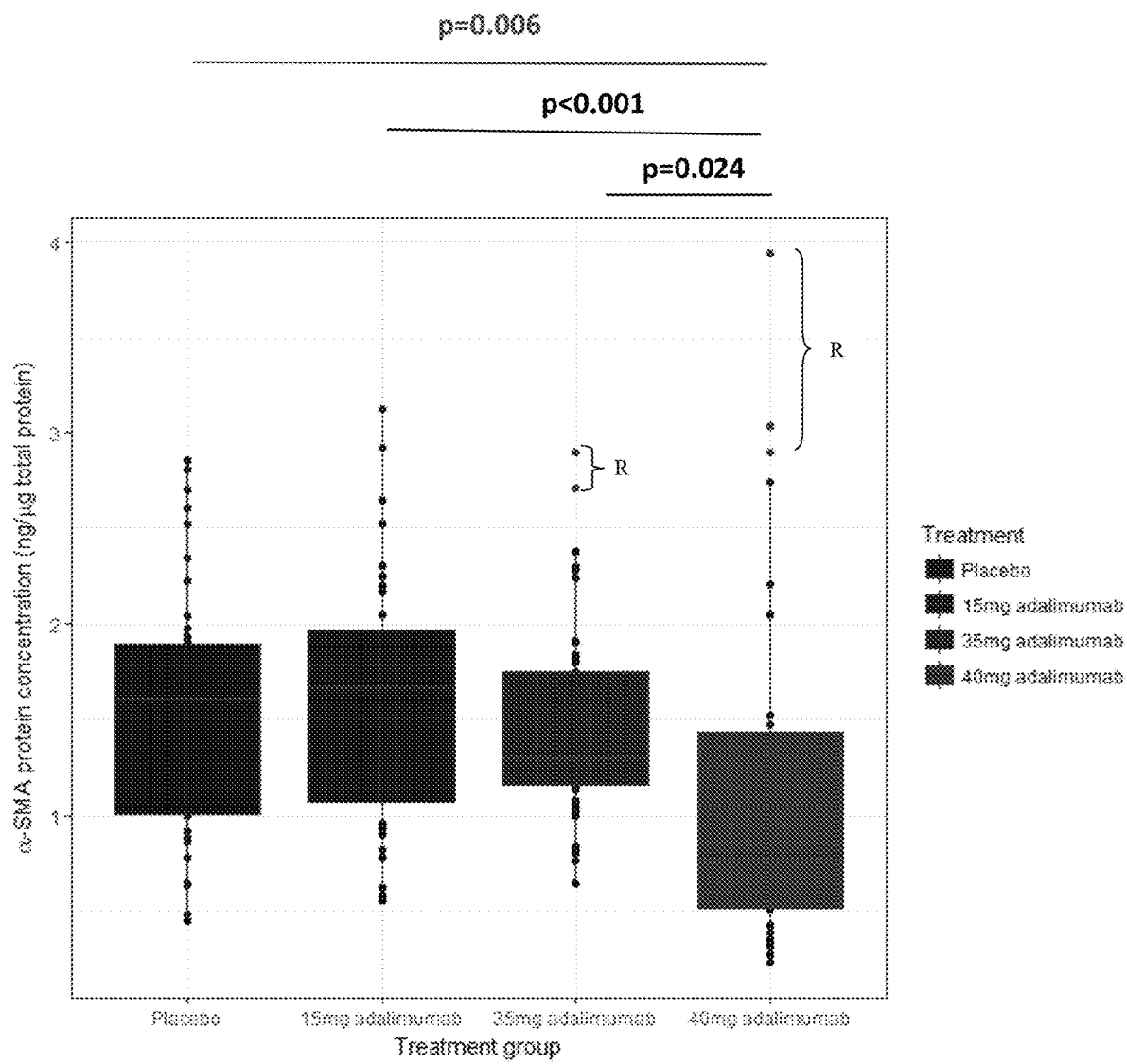
Figure 14A:
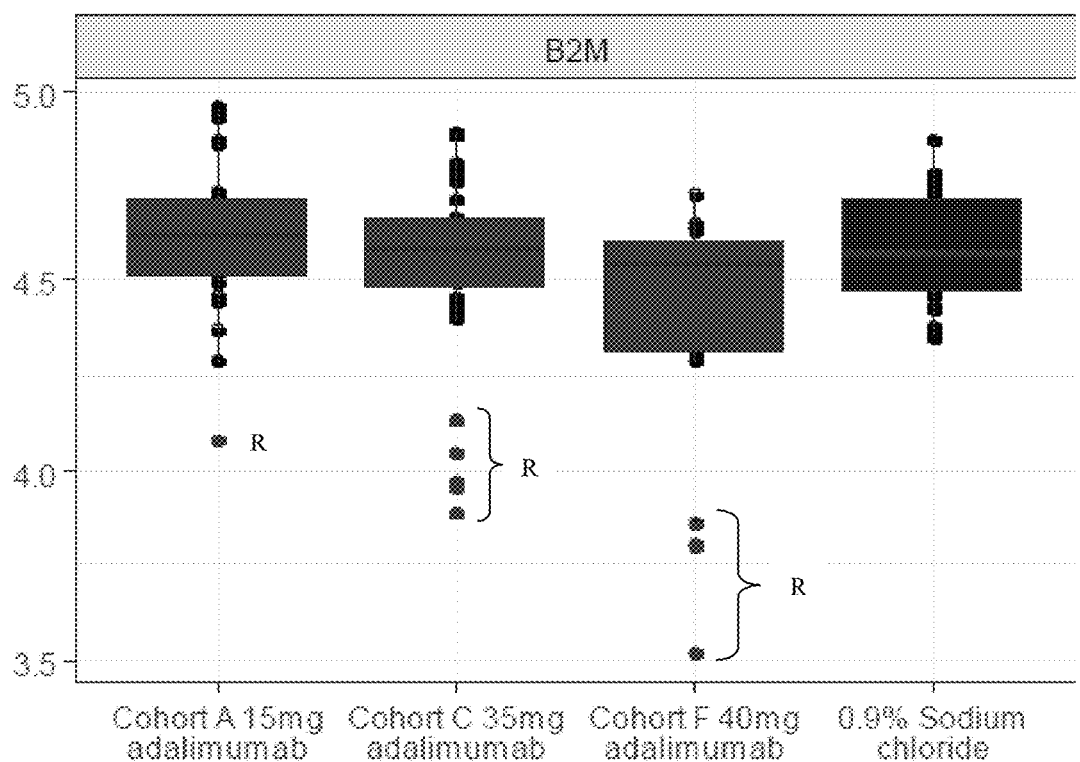
Figure 14B:
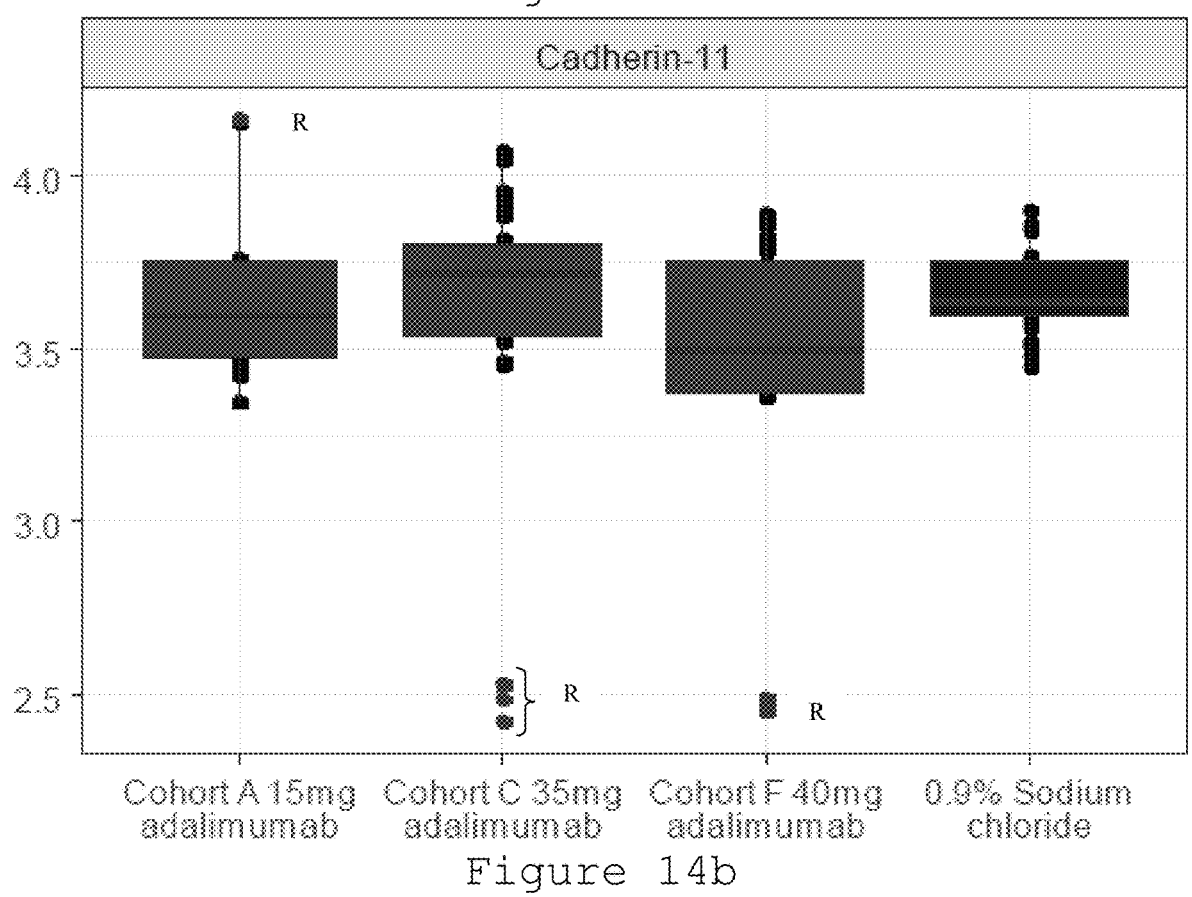
Figure 14C:
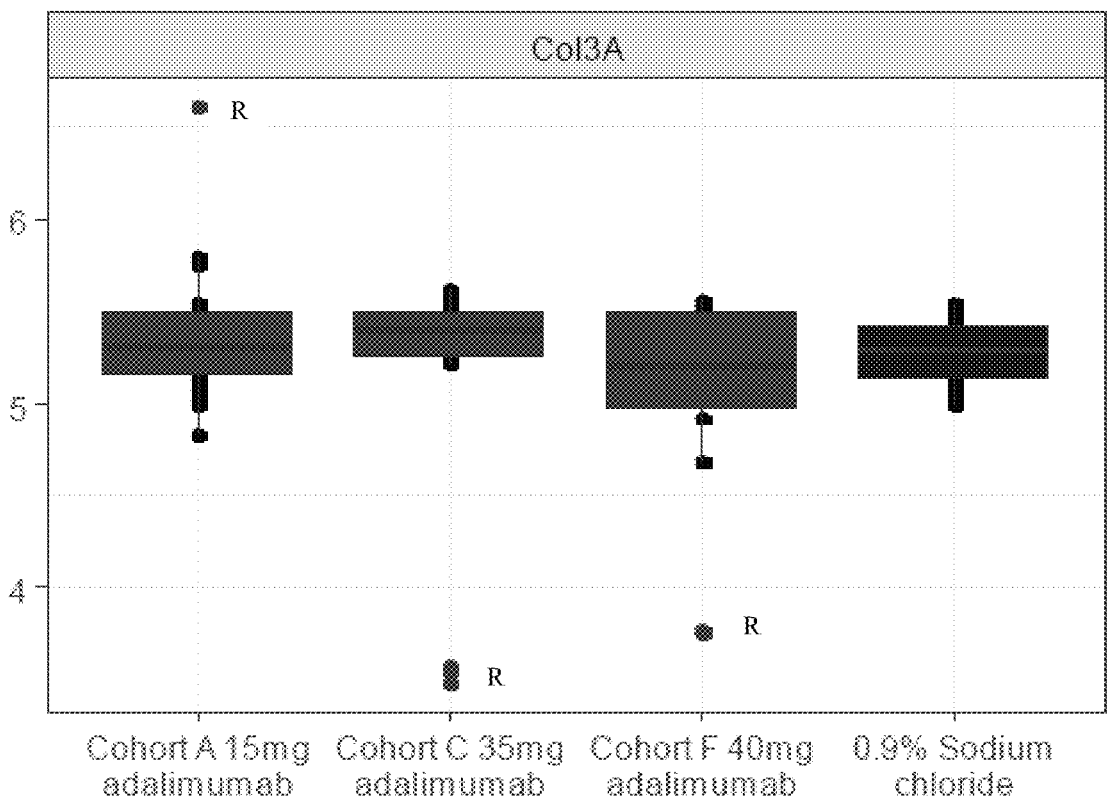
Figure 14D:
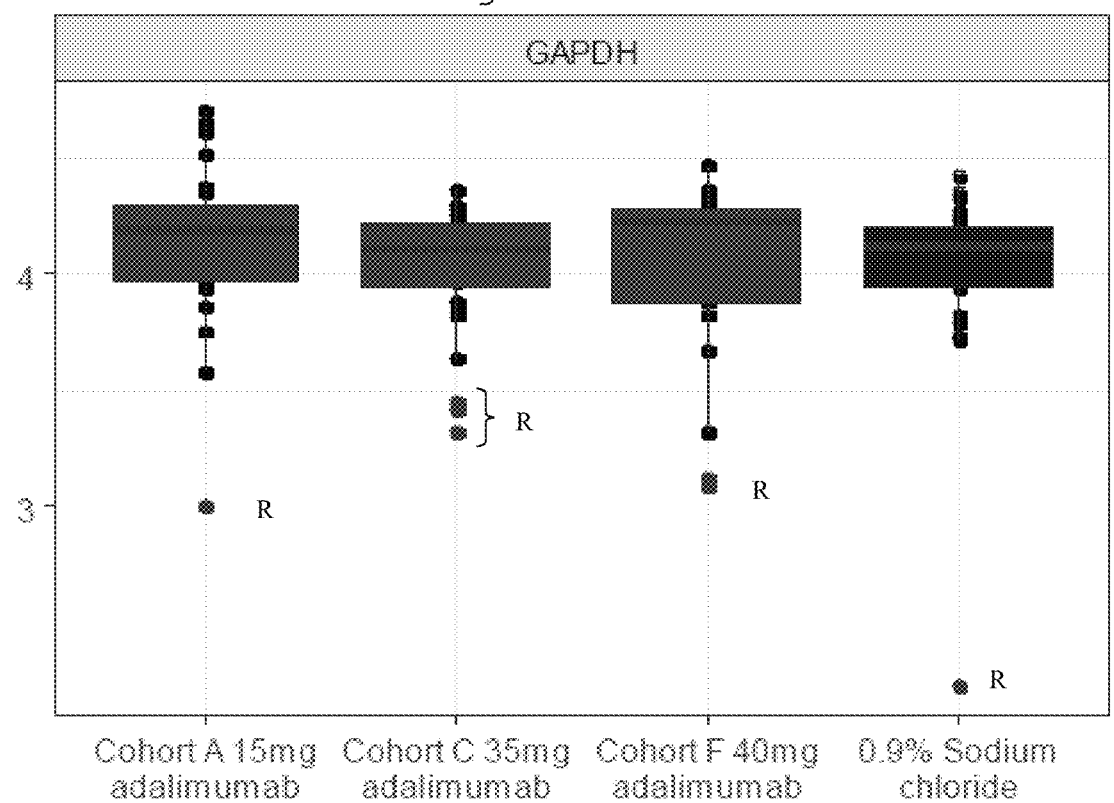
Figure 14E:
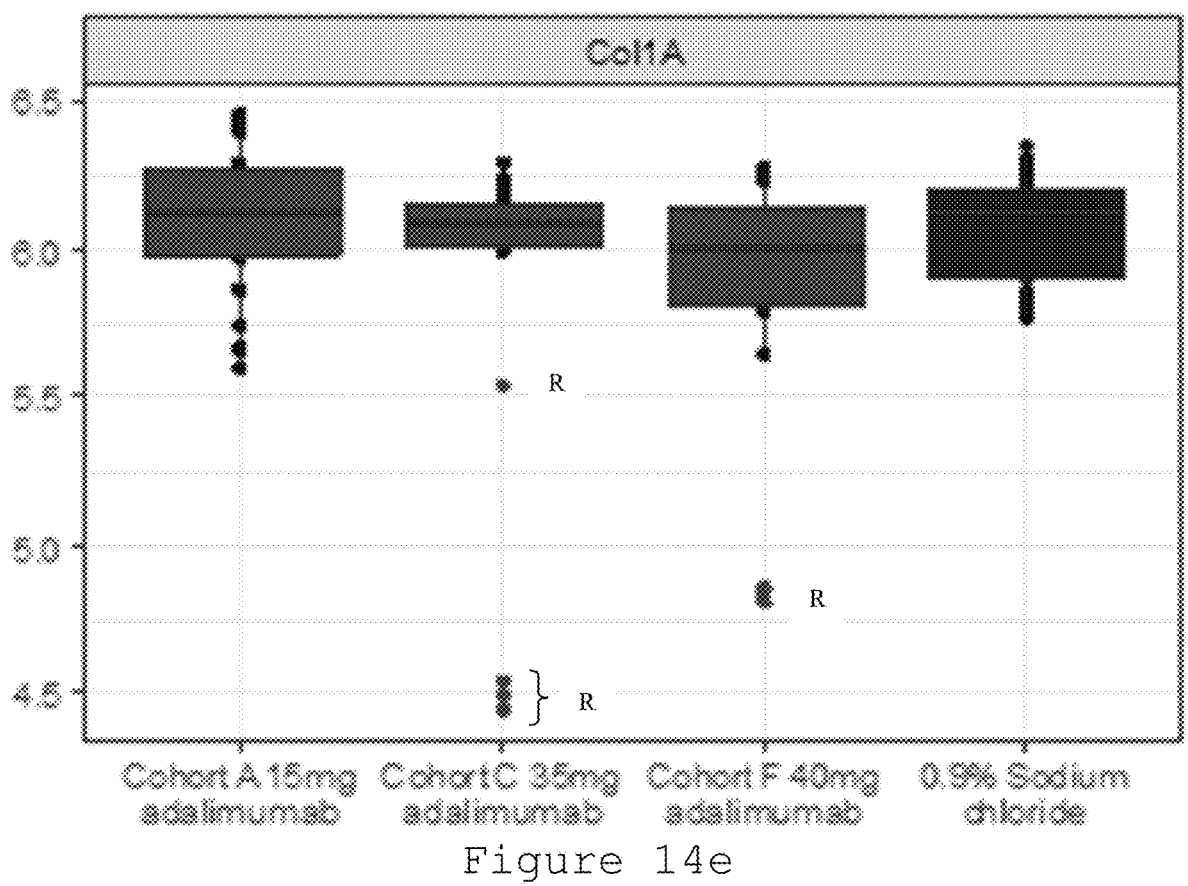
Figure 14F:
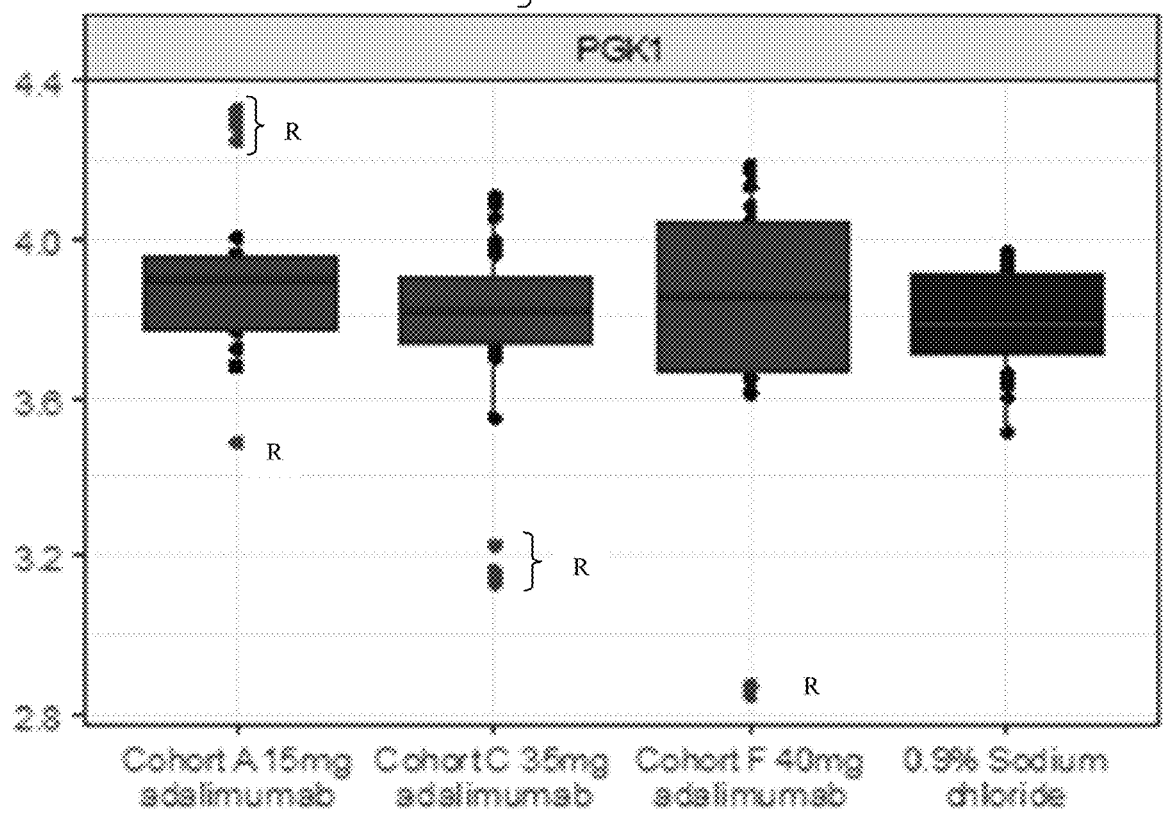
Figure 14G:
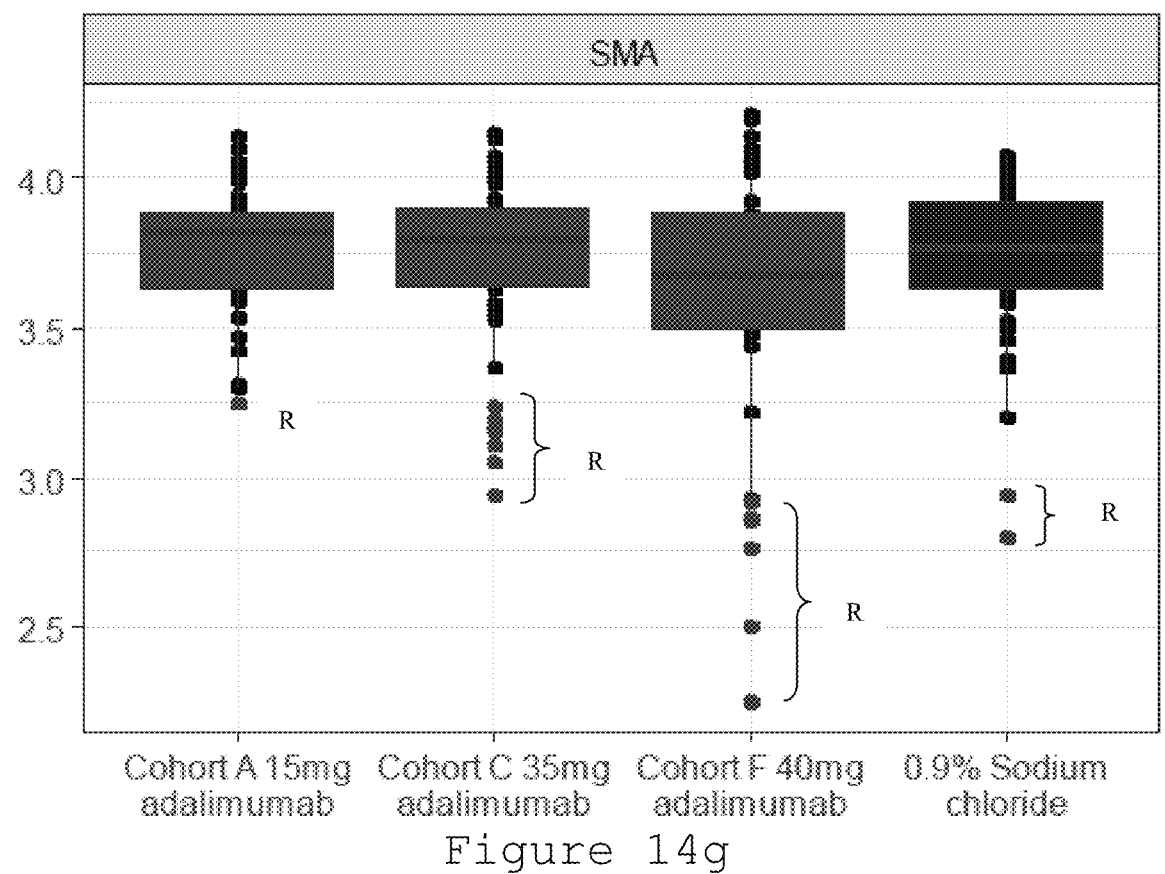

FIG. 13: Downregulation of the α-SMA protein. Box and whiskers plot of α-SMA protein concentration by treatment received. The box represents the inter-quartile range (IQR) and whiskers extend to 1.5 relevant IQR (Tukey boxplot). Data beyond the end of the whisker are plotted and the letter R is adjacent to these data points.

FIG. 14a-14g: Box and whiskers plots of log RNA concentration by treatment received. Y axis is RNA concentration (Log copy number/5μ). Each figure is a separate plot for a gene assessed. The box represents the inter-quartile range (IQR) and whiskers extend to 1.5 relevant IQR (Tukey boxplot). Data beyond the end of the whisker are plotted and the letter R is adjacent to these data points.

Figure 15:
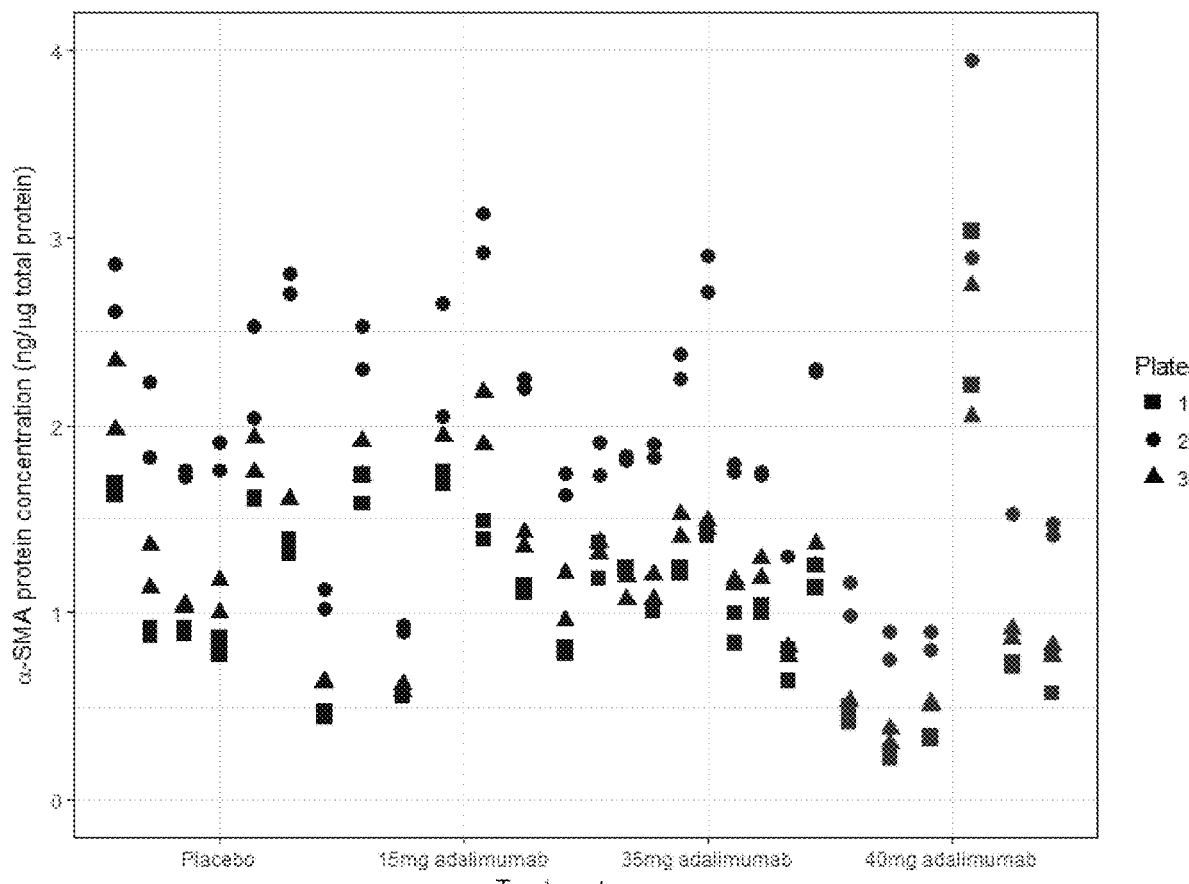

FIG. 15: Scatter plot of α-SMA protein concentration by treatment received. Each group represents one patient analyzed in duplicate on 3 plates. Only one of the patients in the 40 mg cohort failed to respond.

Figure 16:
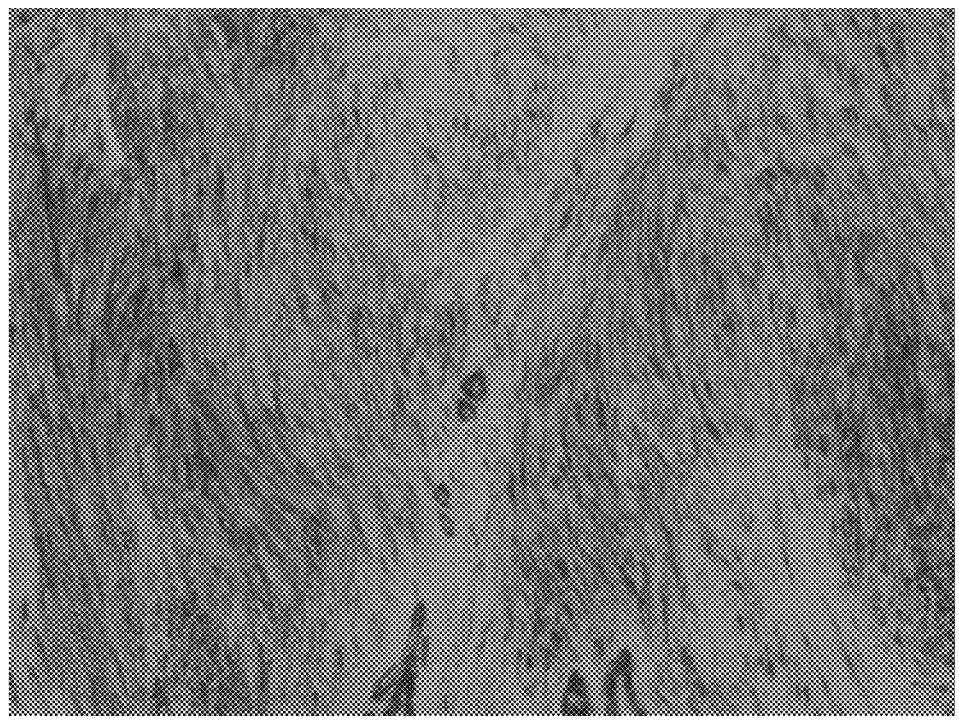
Figure 16:
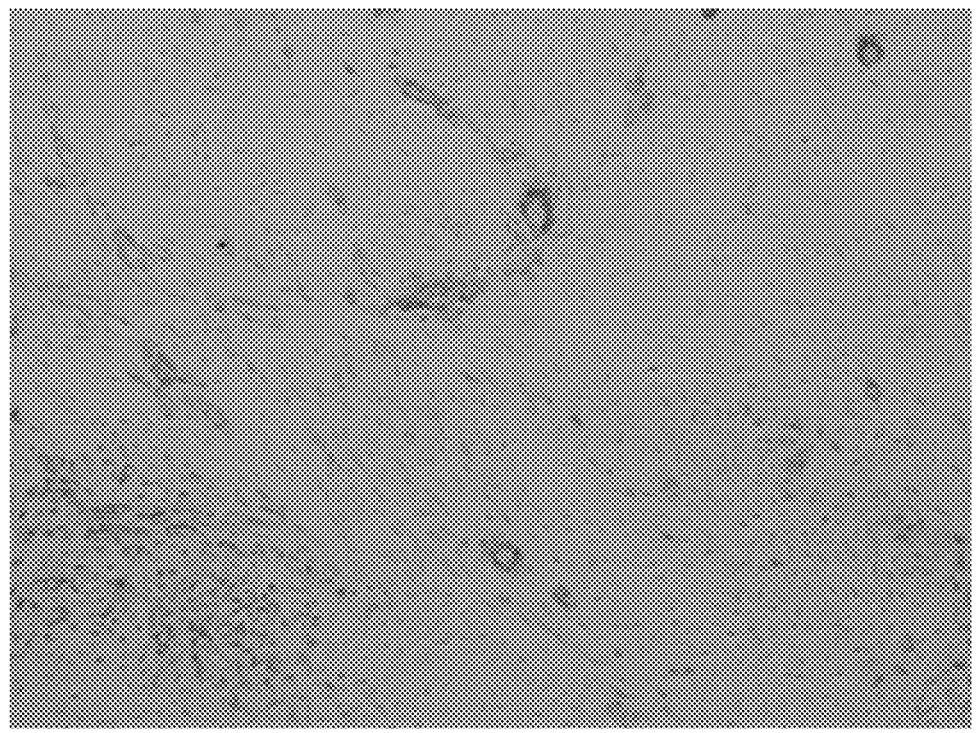

FIG. 16: Representative images for immunohistochemical staining for α-SMA. This is consistent with the significant decrease in α-SMA protein observed in the 40 mg adalimumab dose group (see FIG. 13).

DETAILED DESCRIPTION OF THE INVENTION

The subject invention provides a method of treating an individual afflicted with early stage Dupuytren's disease characterized by the presence of one or more nodules on the individual's hand which comprises injecting into each nodule a pharmaceutical composition comprising an amount of an anti-human TNF antibody or fragment thereof effective to treat the individual, wherein the pharmaceutical composition is in the form of a liquid and between 0.1 ml and 0.6 ml of the composition is in into each nodule.

In one embodiment the pharmaceutical composition is administered using a syringe with a fine needle, the size of which is equal to or greater than 25 gauge.

In alternative embodiments between 0.2 ml and 0.5 ml, between 0.2 and 0.4 ml, or between 0.3 ml and 0.5 ml of the composition is injected. Specifically, 0.3 ml, 0.4 ml or 0.5 ml of the composition is injected.

In alternative embodiments the size of the needle is equal to or greater than 20 gauge, equal to or greater than 22 gauge, equal to or greater than 25 gauge, or equal to or greater than 34 gauge. Specifically the size of the needle may be 25 gauge.

In one embodiment the injection is repeated one or more times at a time interval of no less than six weeks. In alternative embodiments the injection is repeated one or more times at a time interval of no less than 3 months, no less than 4 months, no less than 6 months or no less than 1 year.

In one embodiment, the anti-human TNF antibody or fragment is golimumab, adalimumab, certolizumab pegol or infliximab.

In one embodiment, the anti-human TNF antibody or fragment is golimumab and the amount of golimumab injected into each nodule at any one time is between about 1 mg and about 40 mg. In alternative embodiments the amount of golimumab injected into each nodule at any one time is between about 2 mg and about 40 mg, between about 5 mg and about 40 mg, between about 10 mg and about 40 mg, or between about 20 mg and about 40 mg. Specifically, the amount of golimumab injected into each nodule at any one time is about 40 mg or about 20 mg. In another embodiment, the maximal dosage of golimumab with other site injections is up to about 90 mg.

In one embodiment, a second pharmaceutical composition comprising an anti-human TNF antibody or fragment thereof is administered by subcutaneous injection. In another embodiment, the second anti-human TNF antibody or fragment thereof is the same as the anti-human TNF antibody or fragment thereof injected into the nodule or nodules on the patient suffering from Dupuytren's disease. In another embodiment, the amount of the anti-human TNF antibody or fragment thereof in the second pharmaceutical composition is about 50 mg.

In one embodiment, the anti-human TNF antibody or fragment is adalimumab and the amount of adalimumab injected into each nodule at any one time is between about 5 mg and about 100 mg. In alternative embodiments the amount of adalimumab injected into each nodule at any one time is between about 5 mg and about 40 mg, or between about 10 mg and about 30 mg. Specifically, the amount of adalimumab injected into each nodule at any one time is about 40 mg or about 20 mg.

In one embodiment, the anti-human TNF antibody or fragment is certolizumab pegol and the amount of certolizumab pegol injected into each nodule at any one time is between about 50 mg and about 200 mg. In another embodiment, the amount of certolizumab pegol injected into each nodule at any one time is between about 50 mg and about 130 mg.

In one embodiment, the anti-human TNF antibody or fragment is infliximab and the amount of infliximab injected into each nodule at any one time is between about 50 mg and about 300 mg. In another embodiment, the amount of infliximab injected into each nodule at any one time is between about 50 mg and about 100 mg.

In one embodiment, the method also comprises administering to the individual an amount of one or more human matrix metalloproteinases selected from the group consisting of human metalloproteinase-1 (MMP-1), human metalloproteinase-2 (MMP-2), human metalloproteinase-3 (MMP-3), human metalloproteinase-7 (MMP-7), human metalloproteinase-8 (MMP-8), human metalloproteinase-9 (MMP-9), human metalloproteinase-10 (MMP-10), human metalloproteinase-11 (MMP-11), metalloproteinase-12 (MMP-12, and human metalloproteinase-13 (MMP-13) wherein the amount of such one or more human matrix metalloproteinase when taken together with the amount of the anti-human TNF antibody or fragment increases the effectiveness of treating the individual. In alternative embodiments, the amount of such one or more human matrix metalloproteinases is between 0.01 mg and 10 mg or between 0.01 mg and 2 mg.

In one embodiment, the amount of the one or more human matrix metalloproteinase and the amount of the anti-human TNF antibody or fragment are administered adjunctively and/or concomitantly. In another embodiment, the amount of the one or more human matrix metalloproteinase and the amount of the anti-human TNF antibody are administered sequentially up to 48 hours apart, preferably between 1 hour and 24 hours apart. In one embodiment, the one or more human matrix metalloproteinase is human metalloproteinase-1 (MMP-1).

In one embodiment, the method further comprises administering to the individual an amount of collagenase comprising Xiaflex, wherein the amount of collagenase comprising Xiaflex when taken together with the amount of the anti-human TNFα antibody or fragment increases the effectiveness of treating the individual.

In one embodiment, the method further comprises administering to the individual an amount of bacterial collagenase comprising Xiaflex, wherein the amount of bacterial collagenase when taken together with the amount of the anti-human TNF antibody or fragment increases the effectiveness of treating the individual.

In one embodiment, the method further comprises administering to the individual an amount of a human Cathepsin L, wherein the amount of human Cathepsin L when taken together with (i) the amount of the anti-human TNF antibody or fragment and/or (ii) the amount of one or more human matrix metalloproteinases increases the effectiveness of treating the individual. In another embodiment, the Cathepsin L is HTI-501.

In one embodiment, the pharmaceutical composition is free of citrate.

The subject invention provides a pre-filled syringe which comprises:
a) a pharmaceutical composition in the form of a liquid comprising in a volume between 0.1 ml and 1.0 ml, an amount of an anti-human TNF antibody or fragment thereof effective to treat an individual afflicted with early stage Dupuytren's disease characterized by the presence of one or more nodules on the individual's hand and
b) a fine needle on the syringe, the size of which is equal to or greater than 25 gauge.

In alternative embodiments the volume is between 0.1 ml and 0.6 ml, between 0.2 ml and 0.6 ml, between 0.2 ml and 0.5 ml, between 0.2 ml and 0.4 ml, or between 0.3 ml and 0.5 ml. Specifically, the volume is 0.3 ml, 0.4 ml or 0.5 ml.

In alternative embodiments the size of the needle is equal to or greater than 22 gauge, equal to or greater than 25 gauge, or equal to or greater than 34 gauge. The size of the need may be 25 gauge.

In one embodiment, the anti-human TNFα antibody or fragment is golimumab, adalimumab, certolizumab pegol or infliximab.

In one embodiment, the anti-human TNF antibody or fragment is golimumab and the amount of golimumab is between about 1 mg and about 40 mg. In alternative embodiments the amount of golimumab is between about 2 mg and about 40 mg, between about 5 mg and about 40 mg, between about 10 mg and about 40 mg, or between about 20 mg and about 40 mg. Specifically, the amount of golimumab is about 40 mg or about 20 mg.

In one embodiment, the anti-human TNF antibody or fragment is adalimumab and the amount of adalimumab is between about 5 mg and about 100 mg. In alternative embodiments the amount of adalimumab is between about 5 mg and about 40 mg, or between about 10 mg and about 30 mg. Specifically, the amount of adalimumab as about 40 mg or about 20 mg.

In one embodiment, the anti-human TNF antibody or fragment is certolizumab pegol and the amount of certolizumab pegol is between about 50 mg and about 200 mg. In another embodiment, the amount of certolizumab pegol is between about 50 mg and about 130 mg.

In one embodiment, the anti-human TNFα antibody or fragment is infliximab and the amount of infliximab is between about 50 mg and about 300 mg. In another embodiment, the amount of infliximab is between about 50 mg and about 100 mg.

In one embodiment, the pharmaceutical composition further comprises one or more human matrix metalloproteinases selected from the group consisting of human metalloproteinase-1 (MMP-1), human metalloproteinase-2 (MMP-2), human metalloproteinase-3 (MMP-3), human metalloproteinase-7 (MMP-7), human metalloproteinase-8 (MMP-8), human metalloproteinase-9 (MMP-9), human metalloproteinase-10 (MMP-10), human metalloproteinase-11 (MMP-11), metalloproteinase-12 (MMP-12, and human metalloproteinase-13 (MMP-13). In alternative embodiments the amount of such one or more human matrix metalloproteinases is between about 0.01 mg and about 10 mg or between about 0.01 mg and about 2 mg.

This invention also provides a therapeutic package for dispensing to, or for use in dispensing to, an individual afflicted with early stage Dupuytren's disease, Peyronie's disease and/or frozen shoulder, which comprises:

a) one or more unit doses, each such unit dose comprising:
  i) an anti-human TNF antibody or fragment thereof and/or a soluble TNF receptor and
  ii) an amount of a collagenase preferably Xiaflex
wherein the respective amounts of said anti-human TNFα antibody or fragment thereof and/or soluble TNF receptor and said collagenase preferably Xiaflex in said unit dose are effective, upon concomitant administration to said individual, to treat the individual, and
b) a finished pharmaceutical container therefor, said container containing said unit dose or unit doses, said container further containing or comprising labeling directing the use of said package in the treatment of said subject.

In one embodiment, the pharmaceutical composition is free of citrate. The subject invention also provides a method of treating an individual afflicted with early stage Dupuytren's disease characterized by the presence of one or more nodules on the individual's hand which comprises injecting into each nodule a pharmaceutical composition comprising an amount of a soluble TNF receptor effective to treat the individual, wherein the pharmaceutical composition is in the form of a liquid and between 0.1 ml and 0.6 ml of the composition is injected into each nodule.

In one embodiment, the soluble TNF receptor is a soluble p75 receptor, for example, etanercept.

In one embodiment, the TNF antagonist is abatacept or ORENCIA®. In another embodiment, the TNF antagonist is tocilizumab or ACTEMRA®. In another embodiment, the TNF antagonist is tofactinib or XELJANZ®. In another embodiment, the TNF antagonist is fostamatinib. In another embodiment, the TNF antagonist is remicade.

In one embodiment, the TNF antagonist is a small molecule TNF inhibitor.

In one embodiment, the antagonist is Janus kinase (JAK) inhibitor. In another embodiment, the Janus kinase (JAK) inhibitor is baricitinib.

In one embodiment, the antagonist is a PDE-4 inhibitor. In another embodiment, the PDE-4 inhibitor is apremilast.

In one embodiment, the antagonist is GSK1995057. In another embodiment, the antagonist is mapatumumab. In another embodiment, the antagonist is sirukumab. In another embodiment, the antagonist is vercirnon. In another embodiment, the antagonist is ofatumumab or ARZERRA®. In another embodiment, the antagonist is belimumab or BENLYSTA®.

In one embodiment, the antagonist is a human anti-IFN monoclonal antibody. In another embodiment, the human anti-IFN-alpha monoclonal antibody is MEDI-545.

In one embodiment, the antagonist is a humanized monoclonal antibody. In another embodiment, the humanized monoclonal antibody is epratuzumab.

In one embodiment, the pharmaceutical composition is effective to treat the individual with early stage Dupuytren's disease but not effective to treat an individual with established disease state Dupuytren's disease.

In one embodiment, early stage Dupuytren's disease is defined by the presence of cellular nodules.

In one embodiment, the one or more nodules comprise an aggregate of myofibroblasts and inflammatory cells.

In one embodiment, the one or more nodules are clinically apparent or detectable by (i) visualization by naked eye; (ii) palpation; and/or (iii) an ultrasound scan.

In one embodiment, the invention further comprises treating an individual afflicted with Peyronie's disease or frozen shoulder.

For the foregoing embodiments, each embodiment disclosed herein is contemplated as being applicable to each of the other disclosed embodiments. In addition, the elements recited in the packaging and pharmaceutical composition embodiments can be used in the method and use embodiments described herein.

One surprising aspect of the present invention is that the injection of anti-TNF antibody or fragment would only be effective during the cellular phase, i.e. the period when there are aggregates of myofibroblasts and inflammatory cells. It is currently not contemplated that an injection of anti-TNF antibody or fragment would be effective on the late, relatively acellular phase, of the disease.

An inventive step of the present invention is that anti-TNF would only work during the cellular phase, when there are aggregates of myofibroblasts and inflammatory cells. Anti-TNF would not work on the late, relatively acellular phase of the disease.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat Dupuytren's disease. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "about" in the context of a numerical value or range means ±10% of the numerical value or range recited.

As used herein, an "amount" of a compound as measured in milligrams refers to the milligrams of compound present in a preparation, regardless of the form of the preparation. An "amount of compound which is 40 mg" means the amount of the compound in a preparation is 40 mg, regardless of the form of the preparation. Thus, when in the form with a carrier, the weight of the carrier necessary to provide a dose of 40 mg compound would be greater than 40 mg due to the presence of the carrier.

As used herein, to "treat" or "treating" encompasses, but is not limited to inducing inhibition, regression, or stasis of the disorder and/or disease. As used herein, "inhibition" of disease progression, disease symptoms or disease complications in a subject means preventing, reducing or reversing the disease progression, disease symptoms and/or disease complications in the subject.

Xiaflex is a formulation of two collagenase enzymes co-expressed and harvested from anaerobic fermentation of a phenotypically selected strain of *Clostridium histolyticum* bacterium.

It is understood that where a parameter range is provided, all integers within that range, and tenths thereof, are also provided by the invention. For example, "20-40 mg" includes 20.0 mg, 20.1 mg, 20.2 mg, 20.3 mg, etc. up to 40.0 mg.

Any known anti-human TNF antibody or fragment may be utilized in the implementation of the invention, including TNF antagonists.

Additionally, any known TNF antagonist may be utilized, a broad variety of which are known and disclosed in the art. Optionally, the TNF antagonist may be an antibody, such as a monoclonal antibody or fragment thereof; a chimeric monoclonal antibody (such as a human-murine chimeric monoclonal antibody); a fully human monoclonal antibody; a recombinant human monoclonal antibody; a humanized antibody fragment; a soluble TNF antagonist, including orally available small molecule TNF blocking agents such as thalidomide or analogues thereof or PDE-IV inhibitors; a TNF receptor or a TNF receptor fusion protein, e.g. a soluble TNF receptor or TNF receptor fusion protein. Optionally, the TNF antagonist is a functional fragment or fusion protein comprising a functional fragment of a monoclonal antibody, e.g. of the 15 types mentioned above, such as a Fab, F(ab')2, Fv and preferably Fab. In one embodiment the fragment may be pegylated or encapsulated (e.g. for stability and/or sustained release).

Optionally, a TNF antagonist is provided as a bi-functional (or bi-specific) antibody or bi-functional (or bi-specific) antibody fragment. The bifunctional TNF antagonist antibody or fragment thereof may be, for example, an antibody, such as a monoclonal antibody or fragment thereof, a chimeric monoclonal antibody (such as a human-murine chimeric monoclonal antibody), a fully human monoclonal antibody, a recombinant human monoclonal antibody, a humanized antibody fragment. Where the TNFα antagonist comprises a bifunctional antibody fragment or portion, it is preferably a bi-functional F(ab')2 fragment or divalent ScFv, e.g. a bi-specific tandem di-ScFv. In any case, the bifunctional (or bi-specific) antibody or fragment thereof may comprise as one variable domain (e.g. antigen binding portion), a TNF antagonist (e.g. a TNFα antagonist portion of Infliximab, Adalimumab, Certolizumab, Golimumab, pegol or Etanercept) and as the other variable domain (e.g. antigen binding portion) a second variable domain other than TNFα antagonist. Optionally, the second variable domain may comprise an antibody mobility inhibitor, which may be, for example a domain which binds to an extracellular matrix, e.g. a collagen binder. Thereby, a higher dose of TNF antagonist may be administered since the antibody or fragment thereof will be self-localizing, minimizing systemic uptake and thus systemic side effects. Optionally, the second variable domain may comprise a DAMP antagonist (such as an antagonist for S100A8 and/or S100A9, e.g. as described in U.S. Pat. No. 7,553,488, or HMGB1 antagonist) or an AGE inhibitor (e.g. being variable domains of DAMP antagonist antibody or AGE inhibitor antibody). Methods for the production of bi-functional antibodies, and bi-functional antibody fragments are known in the art, which methods may be applied to the present purpose.

The anti-human TNFα antibody or fragment may be selected, for example, from one or a combination of golimumab, infliximab, adalimumab, or certolizumab pegol or functional fragment thereof. Most preferably, the anti-human TNF antibody is golimumab.

Other TNF antagonists are disclosed in Tracey, 2008, the contents of which are hereby incorporated by reference.

Although some TNF antagonists are optimized for oral administration, they could also be injected with appropriate formulated forms and/or be used orally with collagenase treatment.

The human matrix metalloproteinase is a collagenase.

As used herein, human matrix metalloproteinase refers to both natural forms, forms produced by recombinant DNA technology, which is understood by a person with ordinary skill in the art, and mutated forms having analogous activity. For example, human matrix metalloproteinase can be as found in nature as in Gross, 1962, or it can be in mutated form as in Paladini, 2013, the contents of which are hereby incorporated by reference in its entirety. Human matrix metalloproteinase produced by DNA technology can be made using prokaryotic or eukaryotic cells or other host systems known to those skilled in the art of protein expression, that yield functional enzyme.

Further, as described in Paladini, 2013, it is possible to create a mutated human matrix metalloproteinase, such as mutated MMP-1, wherein the activity can be modulated by the concentration of Ca2+. This can give the ability to control the in vivo activity of the mutated human matrix metalloproteinase, such as mutated MMP-1.

The following chart identifies and briefly describes the different human matrix metalloproteinase.

| Gene | Name | Location | Description |
|---|---|---|---|
| MMP1 | Interstitial collagenase | secreted | Substrates include Col I, II, III, VII, VIII, X, gelatin |
| MMP2 | Gelatinase-A, 72 kDa gelatinase | secreted | Substrates include Gelatin, Col I, II, III, IV, Vii, X |
| MMP3 | Stromelysin 1 | secreted | Substrates include Col II, IV, IX, X, XI, gelatin< |
| MMP7 | Matrilysin, PUMP 1 | secreted | membrane associated through binding to cholesterol sulfate in cell membranes, substrates include: fibronectin, laminin, Col IV, gelatin |
| MMP8 | Neutrophil collagenase | secreted | Substrates include Col I, II, III, Vii, VIII, X, aggrecan, gelatin |
| MMP9 | Gelatinase-B, 92 kDa gelatinase | secreted | Substrates include Gelatin, Col IV, V |
| MMP10 | Stromelysin 2 | secreted | Substrates include Col IV, laminin, fibronectin, elastin |
| MMP11 | Stromelysin 3 | secreted | MMP-11 shows more similarity to the MT-MMPs, is convertase-activatable and is secreted therefore usually associated to convertase-activatable MMPs. Substrates include Col IV, fibronectin, laminin, aggrecan |
| MMP12 | Macrophage metalloelastase | secreted | Substrates include Elasin, fibronectin, Col IV |
| MMP13 | Collagenase 3 | secreted | Substrates include Col I, II, III, IV, IX, X, XIV, gelatin |

Depuytren's Disease

Dupuytren's disease is characterized by the pathological production of collagen and other matrix components that when they contract, lead to flexion deformities of the digits.

The cell responsible for the contraction in Dupuytren's disease and matrix deposition is the myofibroblast. Myofibroblasts characteristically express α-smooth muscle actin (α-SMA) (Skalli 1986; Darby, 2016), which is the actin isoform typical of vascular smooth muscle cells, in addition to the β- and γ-cytoplasmic actins that are traditionally found in fibroblasts.

One of the earliest classifications of Dupuytrens disease was by Luck (1959) into three stages according to the histological appearance Proliferative, Involutional, and Residual. Further sophistication was added by correlating with the clinical findings and ultrastructural features (Rombouts 1989):

Stage I. Early. Clinically the disease is characterized by the presence of nodules on the palmar aspect of the hand but lack of flexion deformities of the digits. Histologically, mitotic figures are seen, indicating the cells are actively proliferating;

Stage II. Active. This stage is characterized by increasing flexion deformity of the digit(s) but not necessarily with the presence of clinically detectable nodules. Histologically the tissue has a fibrocellular appearance characterized by high cellularity but absence of mitoses, indicating that the cells are not dividing; and Stage III. Advanced disease. Clinically the condition is long-standing condition and has not deteriorated over recent months. At the histological level the cord appears fibrous, mainly composed of collagens, with relatively few cells.

This was extended by Lam to include the relative proportion of type III collagen based on the finding that earlier lesions have a higher proportion of type II collagen and this changes to a greater proportion of type I collagen at the later stages of the disease:

Stage I. 35% type III collage,

Stage II. >20% type III collagen, and

Stage III. <20% type III collagen.

The natural history of Dupuytren's is well known, with early palmar nodules progressing to clinically detectable cords that result in increasing flexion deformities of the digits. The majority of authors have based their classification on histological examination of excised tissue. However, since there is general agreement that surgery should only be performed when the joint is flexed (bent) to 30 degrees or more, the staging described is to some extent based on extrapolation.

One of the few groups to study tissues collected at all clinical stages of the disease also classified the disorder into 3 stages (Chiu 1978):

Stage I. Early disease. These specimens comprised nodules from patients with no digital contracture. The tissue comprised proliferating spindle shaped cells that were surrounded by fine granulofibrillary material but there was no increased collagen deposition in the nodule.

Stage II. Active disease. Clinically these patients presented with palmar thickening with associated joint contracture, which on average occurred over 3 years. The nodules comprised mainly of myofibroblasts with very little intervening collagen. The myofibroblasts were characterized by bundles of microfilaments and prominent intercellular junctions. The nodules were associated with cords, which were relatively acellular Stage III. Advanced disease. These patients had progressive joint contracture for more than 3 years. Microscopic examination revealed relatively few cells that were elongated and embedded in stroma comprising a large amount of mature collagen fibres.

Studies on surgically excised specimens from patients with digits flexed to 30 degrees or greater and with functional impairment of the hand show that even in this group of patients, nodules comprising aggregates mainly of myofibroblasts with interspersed inflammatory cells are embedded within the cords and anatomically lie adjacent to the flexed joint (Verjee 2009). Furthermore, patients with more advanced deformities are less likely to have identifiable nodules, corresponding to the advanced stage described by Chiu et al (1979).

For the purposes of this application, the Chiu stages I and II (for practical purposes patients with nodules detectable clinically or by ultrasound scan and flexion deformities of up to 30 degrees at the metacarpophalangeal joint and or the proximal interphalangeal joint) can be included in the group defined as early disease.

The locally produced TNF in the nodules leads to the differentiation of myofibroblasts (Verjee 2013). Furthermore, these myofibroblasts myofibroblasts communicate via intercellular junctions and act as a syncytium (Verhoekx 2013). Anti-TNF led to inhibition of the myofibroblasts phenotype, manifest as reduced contractility, disassembly of α-SMA fibres and reduced expression of the α-SMA protein (Verjee 2003). Anti-TNF inhibits the differentiation of myofibroblasts and also inhibits the activity of existing myofibroblasts.

The ideal treatment for Dupuytren's disease would be one that prevents the development of finger contractures with low recurrence rates as this would preclude the need for costly invasive procedures and offer a cost-effective use of healthcare resources for this very large group of patients.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Background

Figure 1:
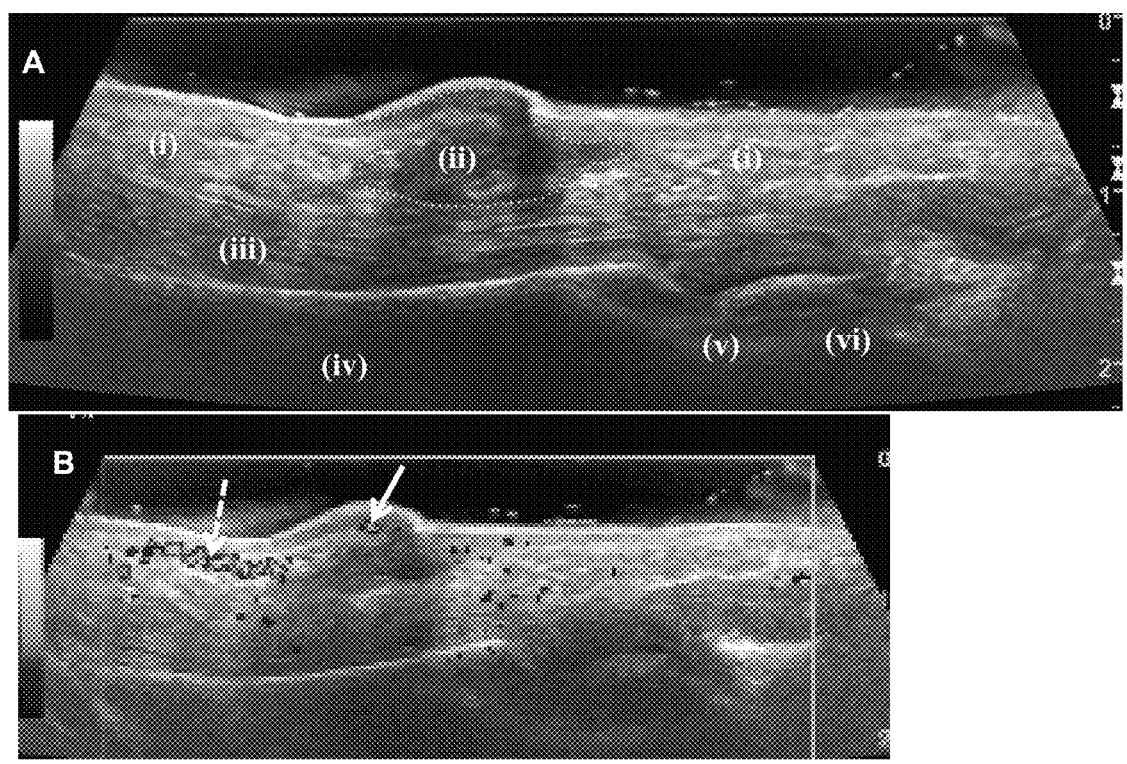
FIG. 1: (A) Gray scale ultrasound image of a patient with early stage Dupuytren's disease showing a well-defined hyopechoeic nodule.

Using surgically excised tissues from patients, it has been demonstrated that development of the myofibroblast is specifically dependent on the local production of TNF and addition of FDA-approved neutralizing antibodies to TNF led to down regulation of the myofibroblast phenotype in vitro. The phase when anti-TNF is likely to be effective would correspond to 'early' and 'active' disease when patients have clearly identified nodules of myofibroblasts and immune cells. Whilst larger nodules can be identified clinically, smaller lesions not easily seen or palpated can be visualized by ultrasound scan (FIG. 1). Further, patients who develop recurrent disease following surgery will by definition have early disease during the initial stages of the recurrence.

The earliest manifestation of Dupuytren's disease is palmar nodules, which can be reliably visualized and measured using an ultrasound scan. FIG. 1 shows an ultrasound image of a patient with early stage Dupuytren's disease showing a well-defined hyopechoeic nodule. Palmar nodules are composed mainly of myofibroblasts. Even in the later stages with digital contractures, the myofibroblasts remain aggregated in histological nodules (Verjee, 2009). It has been shown that scattered throughout the nodules are immune cells, including macrophages and mast cells that secrete pro-inflammatory cytokines. Comparison of the effects of each of these cytokines on myofibroblast precursor cells from the palms of patients with Dupuytren's disease showed that only TNF caused the conversion of palmar fibroblasts from patients with Dupuytren's disease into myofibroblasts at low concentrations ex vivo, whilst these cytokines had the opposite effect on non-palmar fibroblasts from the same patients and on palmar fibroblasts from normal individuals. In contrast, TGF-β acts indiscriminately on all types of fibroblasts (Verjee 2013). This is important as the fibrotic process that occurs in Dupuytren's disease is limited to the palm of genetically susceptible individuals. A genome-wide association study (GWAS) highlighted the role of Wnt signaling in Dupuytren's disease (Dolmans 2011). It was found that TNF, at levels found in freshly disaggregated Dupuytren's tissue, led to the differentiation of palmar dermal fibroblasts only from individuals genetically susceptible to Dupuytren's disease via the Wnt signaling pathway by inhibiting GSK-3β11 (Verjee 2013). This cross-talk between TNF and Wnt signaling has previously been described only in pre-adipocytes.

Results and Discussion

Anti-TNFs such as adalimumab can be accurately delivered into the nodule to the target cells. It is also demonstrated that Dupuytren's myofibroblasts function as a syncytium (Verhoekx, 2013). Hence, in the event there is incomplete penetration of the adalimumab throughout the nodule, downregulation of the contractility of some cells will indirectly but profoundly affect their neighbors. This effect will be magnified since in the absence of tension, myofibroblasts disassemble their α-SMA stress fibres within minutes (Hinz, 2001).

Dupuytren's disease is a localized inflammatory condition and macrophages that secrete the TNF responsible for the development and contractility of myofibroblasts are co-located in the nodules (FIGS. 2 and 3) (Verjee, 2013).

Freshly disaggregated cells from Dupuytren's nodules secrete TNF (mean±SD: 78±26 pg/ml) and variable amounts of TGF-β1 (236±248 pg/ml; range, 4-852 pg/ml) (FIG. 4). TGF-β1 is known to drive the development of myofibroblasts and cultured myofibroblasts upregulate its production in an autocrine manner. Previous studies were only based on cells cultured up to passage 4. However, inventors demonstrated that cells cultured to passage 2 secreted very little TNF (4±4 pg/ml) but produced nearly three times more TGF-β1 (654±158 pg/ml) than fresh tissue.

The effects of recombinant cytokines and on dermal fibroblasts from the palm of patients with Dupuytren's disease (PF-D), non-palmar fibroblasts from Dupuytren's patients (NPF-D) and palmar fibroblasts from non-Dupuytren's patients were examined and the inventors found that TGF-β1 increased the contractility of all 3 types of fibroblasts at concentrations of 1-10 ng/mL, which is in excess of the range in fresh tissue (FIG. 5). Global inhibition of TGF-β1 is undesirable due to its role in a wide range of physiological processes (Varga, 2009) and increased inflammation, tumor promotion, and cardiac toxicity seen in animal studies (Budd, 2012). Furthermore, to date TGF-β1 inhibition has not been effective in clinical late phase trials for fibrotic disorders (Varga, 2009; Hawinkels, 2011).

In contrast, TNF converted only PF-D into myofibroblasts whereas NPF-D and PF-N became less contractile (FIG. 5). The optimal dose for conversion of palmar fibroblasts from Dupuytren's patients was 50-100 pg/ml, similar to the amount found in Dupuytren's tissue (78±26 pg/ml). Therefore, TNF therapy in the claimed methods specifically target the cells responsible for Dupuytren's disease.

It was found that of all the anti-TNF preparations approved by the FDA for subcutaneous administration, adalimumab or golimumab were the most effective in down-regulating Dupuytren's myofibroblast phenotype (FIG. 11) (Verjee, 2013). Golimumab led to dose-dependent inhibition of myofibroblast contractility (FIG. 7) with disassembly of their contractile apparatus (FIG. 8). TNF inhibition also reduced expression of the myofibroblast marker α-SMA (FIG. 9) (Verjee, 2013).

It was found that TNF directly controls myofibroblast differentiation via the Wnt/β-catenin signaling pathway (Verjee, 2013). This is consistent with a recent genome-wide association study (GWAS) that demonstrated that Wnt signaling is involved in Dupuytren's disease (Dolmans, 2011). The reason for the selective effect of TNF on palmar fibroblasts from Dupuytren's patients may in part be due to their higher expression of TNF receptors, in particular TNFR2 (FIG. 10).

Global increase was not observed in TNFR1/2 in Dupuytren's patients, with non-palmar fibroblasts exhibiting levels similar to those from individuals without Dupuytren's disease (FIG. 10).

Therefore, TNF is a valid therapeutic target for downregulating the phenotype of existing myofibroblasts and preventing the development of new myofibroblasts. In addition, adalimumab or golimumab were highly effective in vitro There is no validated measure of regression of nodules in patients with early Dupuytren's disease. Others have relied on subjective assessment of ease of injection during subsequent steroid injections (Ketchum, 2000) or clinical impression of nodule size, hardness or number following radiotherapy (Seegenschmiedt, 2001).

The expression of α-SMA mRNA is used as the primary outcome measure of efficacy adalimumab in downregulating myofibroblast activity. This is a reliable measure of myofibroblasts phenotype (FIG. 9) (Verjee, 2013). It has the additional advantage of enabling the use of primary cells from the excised nodules, without the need for expansion in cell culture. In the same patients nodule hardness is quantified by tonometry and nodule size and vascularity using ultrasonography (FIG. 1A,1B). Data on 25 patients with early disease compared with age and sex matched health volunteers demonstrate that Dupuytren's nodules and the overlying palmar tissues are significantly firmer than the corresponding sites in controls (Table 1). Ultrasonography as a measure of disease activity has been demonstrated to be a reliable measure in rheumatoid patients (Seymour, 2012).

TABLE 1

Comparison of patients with early Dupuytren's disease and age- sex-matched controls

|  | Early Dupuytren's (mean ± SD) | Normal (mean ± SD) | P |
|---|---|---|---|
| PROM (MHQ) | 80 ± 17 | 93 ± 8 | 0.0058 |
| Extensor deficit (MCPJ + PIPJ) | 11° ± 20° | 1° ± 2° | 0.0018 |
| Tonometry | 53 ± 8 | 32 ± 3 | <0.0001 |

In data shows that golimumab reduces myofibroblast contractility in a dose-dependent fashion (FIG. 7) and anti-TNF also reduces the expression of α-smooth muscle actin (α-SMA) protein (FIG. 9). Ultrasound guidance preferably is used to inject adalimumab or saline directly into Dupuytren's nodules in patients with established disease and finger contractures 2 weeks before they are scheduled to undergo surgery.

Expression of α-SMA was measured using Western blotting. In vitro it was found that treatment with 10 μg/ml of anti-TNF led to reduction in the expression of α-SMA.

Example 2

A randomized trial in patients with Dupuytren's disease is performed. It is determined that direct injection of adalimumab resulted in a significant ($p \leq 0.05$) dose-dependent down regulation of α-SMA protein by myofibroblasts.

Outcome Measures

Primary outcome measure—expression of mRNA for α-SMA measured using RT-PCR. Nodules in controls patients are injected with saline. This provides a quantitative readout.

Secondary outcome measures—expression of α-SMA protein measured using electrochemiluminescence (Meso Scale Discovery). Expression of mRNA for COL-1A, COL_3A, cadherin 11 measured using RT-PCR. Nodule size is measured and vascularity (FIGS. 1A and 1B) using ultrasound scan before injection and just before surgery. In addition, nodule hardness is measured by tonometry, grip strength using a Jamar meter and range of motion of the affected digit using a goniometer. Patients identify their most restricted activity and score their impairment on a scale of 0-10 before injection and immediately before surgery (Engstrand, 2009).

Additional clinical outcome measures—are obtained before injection and immediately before surgery include patient reported outcome measure of hand function (Michigan Hand Questionnaire—MHQ) and the Disabilities of the Arm, Shoulder and Hand (DASH). Utilities are assessed using EQ-5D-5L. The choice of the clinical outcome measures used is based on a systematic review of the literature (Ball, 2013).

Dosage

The approved dose of adalimumab for patients with rheumatoid arthritis is 40 mg in 0.8 ml or 0.4 ml, depending on the formulation, administered subcutaneously every 4 weeks. This may be increased to 80 mg, with 40 mg injected at separate anatomical sites. In this example, adalimumab is injected into the most prominent nodule in the palm preferably identified clinically by an ultrasound scan. The first group is injected with a dose of 15 mg of adalimumab in a total volume of 0.3 ml (n=6). The second group of patients are injected with 35 mg of adalimumab in a total volume of 0.7 ml (n=12). The third group is injected with 40 mg of adalimumab in 0.4 ml (n=6). For each group, patients were randomized 4:1 to receive an equivalent volume of saline. Applicants found that 40 mg (0.4 ml) of golimumab can be reliably injected into the nodules without significant spillover into the surrounding tissue. However, injection of 0.7 ml was associated with significant egress out of the nodule into the surrounding tissues.

Using surgically excised Dupuytren's tissue 0.4 ml can be reliably injected into a nodule without significant spill over into the surrounding tissues. Alternatively, between 0.1 ml and 0.6 ml can be injected into each nodule or between 0.2 ml and 0.4 ml can be injected into each nodule or between 0.2 ml or 0.3 ml can be injected into each nodule or 0.3 ml can be injected into each nodule without significant spill over into the surrounding tissue. The lowest dose minimizes the risk of adverse events as well as reduces the cost of the therapy in the long term. Furthermore, spill over into the surrounding tissues was associated with lack of efficacy. Therefore, patients injected with 35 mg adalimumab in 0.7 ml did not show down regulation of the myfibroblasts as evidenced by α-SMA protein expression, whereas 40 mg in 0.4 ml resulted in significant reduction of α-SMA protein within 2 weeks of a single injection in 5 of 6 patients. 15 mg of adalimumb in 0.3 ml remained confined to the nodule when injected but was ineffective, indicating that this dose was too low.

Volumes of adalimumab or saline greater than 0.3-0.4 ml were associated with less pain than the larger volume of 0.7 ml and therefore is likely to be more acceptable to patients, especially if repeated injections are required. The preparation of adalimumab where excipients including citrate were absent (40 mg in 0.4 ml) was associated with significantly less pain. This would be consistent with previously published findings that subcutaneous injection of citrate containing solutions is more painful (Laursen 2006).

A first control group is injected with 0.3 ml of saline into the most prominent nodule in the palm. A second control group is injected with 0.7 ml of saline into the most prominent nodule in the palm. A third control group is injected with 0.4 ml of saline into the most prominent nodule in the palm.

A control is used to ensure that injecting fluid into the nodule in itself does not affect outcome. Therefore, patients in the placebo group are injected with the equivalent amount of saline solution (a randomization of 1 control:4 active treatment).

Procedure of Example

The injections are preferably administered either in a vial and transferred to a syringe or in a prefilled syringe under ultrasound guidance and are blinded regarding the injection agent and whether the patient is receiving a subcutaneous injection.

Tissue sample collection and analysis:

The excised tissue collected at surgery 2 weeks after injection. Patient's nodules are removed by surgery in all patient groups. The nodule is dissected, frozen and homogenized and assayed for total α-SMA protein expressed as μg per mg of total protein. Total copy numbers of the respective mRNA were also determined and normalized to two house keeping genes (B2M and GAPDH).

Schedule

Table 2 shows a summary of the schedule for Example 2.

TABLE 2

Summary of schedule for dose response:

| Procedure | Time in mins | Screening Visit 1 | Baseline Visit 2 Week 0 | Visit 3 Week 2 | Visit 4 Week 2 post-surgery | Visit 5 Week 12 post-surgery |
|---|---|---|---|---|---|---|
| Visit window | | | | ±3 days HAND | ±1 week | ±4 weeks |
| Informed consent | 20 | X | | SURGERY | | |
| Demographics | 5 | X | | | | |
| Medical history | 5 | X | | | | |
| Concomitant medications | 5 | X | X | X | X | X |
| Physical examination | 5 | | X | | | |
| Chest X-Ray | 20 | X | | | | |
| Blood for screening | 5 | X | | | | |
| Blood for research | 5 | | X | X | | |
| Dupuytren's assessment, inc. range of motion | 15 | | X | | | |
| Eligibility assessment | 5 | X | X | | | |
| Health questionnaire | 5 | | X | | | X |
| Nodule hardness (tonometry) | 5 | | X | X | | |

TABLE 2-continued

Summary of schedule for dose response:

| Procedure | Time in mins | Screening Visit 1 | Baseline Visit 2 Week 0 | Visit 3 Week 2 | Visit 4 Week 2 post-surgery | Visit 5 Week 12 post-surgery |
| --- | --- | --- | --- | --- | --- | --- |
| Ultrasound imaging | 15 | | X | X | | |
| Digital photograph of palm | 2 | | X | X | X | |
| Randomisation | | | X | | | |
| Topical anaesthetic and Injection of study drugs or placebo | 40 | | X | | | |
| Injection questionnaire | 5 | | X | | | |
| Adverse event assessment injection site assessment | 5 | | X | X | | |
| Adverse event assessment Surgery site assessment | 5 | | | | X | X |
| Total in minutes | | 65 | 112 | 37 | 12 | 15 |

Inclusion criteria:
The participant may enter the trial if:
participant is willing and able to give informed consent for participation in the study;
participant is Male or Female, aged 18 years or above;
participant is diagnosed with DD affecting the fingers resulting in flexion deformities of ≥30° at the metacarpophalangeal joint and or the proximal interphalangeal joint with impaired hand function and awaiting surgery;
the DD nodule to be treated is be distinct and identifiable;
female participants of child bearing potential, and male participants whose partner is of child bearing potential, are willing to ensure that they or their partner use effective contraception throughout the treatment period and for 5 months following the last research injection. Acceptable methods of contraception include: a combination of male condom with either cap, diaphragm or sponge with spermicide (double barrier methods), injectables, the combined oral contraceptive pill (at a stable dose for at least 3 months before entering the study), an intrauterine device, vasectomised partner, or true sexual abstinence (when this is in line with the preferred and usual lifestyle of the participant);
participant obtains results from safety screening tests within normal ranges within 8 weeks of enrollment, with the exception that an earlier clear CXR result may be used where this is in accordance with the time frames of local standard procedures for anti-TNF screening;
participant is able (in the Investigators opinion) and willing to comply with all study requirements;
participant is willing to allow his or her general practitioner to be notified of participation in the study; and
participant has sufficient language fluency to ensure informed consent is obtained and to complete the questionnaires pertaining to hand function.

The participants selected for this trial were chosen as they would be eligible for surgery but were nonetheless representative of early stage disease as they all had easily identifiable nodules which contained substantial numbers of cells.

Exclusion criteria:
The participant may not enter the trial if any of the following apply:
participant has previously had fasciectomy, dermofasciectomy, needle fasciotomy, collagenase injection, steroid injection or radiotherapy to treat Dupuytren's disease in the digit concerned;
female participant who is pregnant, lactating or planning pregnancy during the course of the study and for 5 months following last injection;
male participant who is planning a pregnancy during the course of the study and for 5 months following last injection;
significant renal or hepatic impairment;
scheduled elective surgery or other procedures requiring general anesthesia during the study other than the scheduled Dupuytren's surgery;
participant has been diagnosed with cancer, is terminally ill or is inappropriate for placebo medication;
participant has a systemic inflammatory disorder such as RA or inflammatory bowel disease;
participant has any other significant disease or disorder which, in the opinion of the Investigator, may either put the participants at risk because of participation in the study, or may influence the result of the study, or the participant's ability to participate in the study;
participant has participated in another research study involving an investigational medicinal product in the past 12 weeks;
participant has known allergy to any anti-TNF agent.
participant has HIV or hepatitis B or C;
participant has is known to nave an infection or history of repeated infections;
participant has history of Tuberculosis (TB);
participant has Multiple Sclerosis (MS) or other demyelinating disease;
participant has history of local injection site reactions;
participant has needle phobia;
participant has moderate or severe heart failure;
participant is being treated with coumarin anticoagulants, such as warfarin;
participant has known lung fibrosis (thickening of lung tissue);
participant has been treated with concomitant biologic DMARDS;
participant has received a live vaccine within the previous 4 weeks. Participants may receive concurrent vaccinations but must avoid the use of live vaccines for 12 weeks after their last injection;
participant has received parenteral steroid within the previous 6 weeks;
if participant has epilepsy or a known allergy to tetracaine, they may take part in the study but will not receive Ametop gel as a local anaesthetic; and participants with a known allergy to lidocaine or prilocaine will not receive lidocaine/prilocaine cream/EMLA cream as a local anaesthetic.

Example 3

Clinical Trial A

A clinical trial was performed. The patients in this trial were (1) afflicted with relatively early stage Dupuytren's disease, (2) had at least one distinct nodule, and (3) were already scheduled for surgical excision of the diseased tissue. Each patient's nodule was identified clinically and also by ultrasound scan.

The patients were randomized to 3 cohorts including 6 treatment groups. The age, severity and duration of disease was similar in all treatment groups. Each patient was injected with a solution comprising adalimumab and carrier or saline. Specifically, one nodule on each patient was injected with one of the formulations.

Two weeks after injection, patients underwent surgical excision and the tissue was analyzed for biomarkers of fibrosis. All participants and assessors were blinded.

The cohorts and treatment groups are as follows:

| Cohort | Treatment Group | Formulation administered | Number of patients |
|---|---|---|---|
| A | 1 | 15 mg adalimumab in 0.3 ml carrier | 6 |
|  | 2 | 0.3 ml saline | 2 |
| C | 3 | 35 mg adalimumab in 0.7 ml carrier | 9 |
|  | 4 | 0.7 ml saline | 3 |
| F | 5 | 40 mg of adalimumab in 0.4 ml | 6 |
|  | 6 | 0.4 ml saline | 9 |

In treatment groups 1 and 3, an adalimumab formulation comprising 40 mg adalimumab in 0.8 ml of carrier from AbbVie® was used. In treatment group 5, an adalimumab formulation comprising 40 mg adalimumab in 0.4 ml of carrier from AbbVie® was used. Treatment groups 2, 4, and 6 were the placebo groups.

Volume of Injections

The ex vivo studies on excised Dupuytren's nodules showed that the maximum volume that could be accommodated within a nodule was 0.3-0.4 ml. Injection of higher volumes were associated with egress of the fluid outside the nodule. During this trial when injecting 0.7 ml, some of the material leaked out into the subcutaneous space outside the nodule. During the course of this example, a new formulation of adalimumab became available which possessed doubled the concentration (40 mg in 0.4 ml) and also removed many of the excipients, including citrate, from the formulation. Injections of citrate buffers are well known to be associated with increased pain (Laursen, 2006). Therefore, based on our ex vivo injection data and observations during the cohorts A and C of this example, it was decided to proceed to cohort F using the new formulation of adalimumab. This has the benefit of less pain as shown in FIG. 12. Patients reported high levels of pain associated with 0.7 ml of adalimumab solution and 0.7 ml of saline. The adalimumab administered in treatment group 3 was particularly painful to patients due to the presence of the excipients in the carrier solution.

Measured outcomes included mRNA levels of α-smooth muscle actin (α-SMA), collagens I and III, and cadherin 11. Levels of α-SMA actin was measured using a chemiluminescence assay (Mesoscale Discovery) that has a linear range 0.025-12 ng/mg total protein. Samples were also taken for immunohistochemical staining for α-SMA. There were no statistical difference found in levels of the mRNA for any of the proteins relative to control saline injections (FIG. 14a-14g). However, there were statistically significant differences in levels of the α-SMA protein, the key biomarker of myofibroblasts and fibrosis. Specifically, the levels of α-SMA protein (ng α-SMA per μg total protein±SD) were as follows:

| Treatment Group | levels of α-SMA protein (ng α-SMA per μg total protein ± SD) |
|---|---|
| Placebo (2, 4 and 6) | 1.51 ± 0.65 |
| 1 | 1.60 ± 0.67 |
| 3 | 1.44 ± 0.48 |
| 5 | 1.09 ± 0.89 |

FIG. 15 shows a breakdown of patient level data showing that all but one of the 6 patients in treatment group 5 (the 40 mg adalimumab cohort) responded.

Patients receiving the 40 mg adalimumab preparation (treatment group 5) and lower volumes (treatment groups 1, 2 and 6) reported lower pain scores after the injection (FIG. 12).

Patients receiving 40 mg of the new adalimumab formulation (treatment group 5) demonstrated a significant down regulation of alpha-smooth muscle protein levels (FIG. 13). An analysis showed significant differences between treatment group 5 and the placebo group (saline) and other dose cohorts. Compared to placebo, the protein levels decreased by approximately 27% in the 40 mg of adalimumab treatment group (treatment group 5). There is a relatively small difference in the dose of adalimumab in the 35 mg adalimumab administration (treatment group 3) and the 40 mg adalimumab administration (treatment group 5). Therefore, the data suggests that adalimumab must be confined to the nodule to be efficacious. One could reasonably extrapolate to say that systemic administration or adalimumab would be ineffective for Dupuytren's disease. This data demonstrates that Dupuytren's disease is a localized inflammatory disease, unlike other indications for anti-TNF therapy e.g. inflammatory arthritis and inflammatory bowel disease. This data shows that anti-TNF would only be effective for early stage Dupuytren's disease if injected directly into the nodule but not if administered systemically.

Administration

The 40 mg adalimumab in 0.4 ml preparation is available in pre-filled syringe from AbbVie®. The diameter of the needle, which is welded to the syringe barrel, is very fine, presumably to reduce pain associated with subcutaneous injection. However, the needle diameter was too small to allow effective administration of adalimumab through the relatively dense tissue of the Dupuytren's nodule. This was because, inter alia, very high pressure was required, which risks denaturing the antibody. The high pressure was also associated with increased pain in the patient. It was found that a 25 gauge needle is ideal for injecting an adalimumab solution into Dupuytren's nodular tissue.

Conclusion

The intralesional 15 mg dose of adalimumab was not effective in down regulating the myofibroblast phenotype. During injection of 35 mg in 0.7 ml of solution it was apparent that some of the preparation was spilling out of the nodule into the subcutaneous tissues. Therefore, it is likely that the local drug levels were insufficient to have an effect.

However, 40 mg of adalimumab 0.4 ml solution (treatment group 5) remained confined to the nodule and effectively down regulated the myofibroblast phenotype as shown by expression of α-SMA protein.

The lower volume and absence of excipients (such as citrate) in the formulation administered to treatment group 5 was associated with lower pain scores. This is likely to result in higher patient acceptability of the treatment.

In summary, it has been shown that anti-TNF therapy is only effective if it is administered directly into the nodule and it remains confined to the nodule. An effective dose is 40 mg of adalimumab, but this dose should be administered in a volume of 0.4 ml or less. It has been demonstrated that 35 mg of adalimumab in 0.7 ml total solution was not efficacious. This is likely because the nodule can only accommodate 0.3-0.4 ml of solution and any larger amounts of solution will likely result in adalimumab spilling out of the nodule. This would suggest that systemic administration of anti-TNF would not be effective. It has also been shown that a high gauge syringe must be used to inject an anti-human TNF antibody into a nodule. The fine needle supplied on pre-filled syringes from AbbVie® is not suitable for injecting anti-human TNF antibodies into nodules because it requires very high pressure to infiltrate the fibrous nodule, which makes it difficult to administer, risks denaturing the protein and results in increased pain. Finally, it has been shown that certain excipients, such as citrate, in certain preparations of adalimumab is associated with more pain. Also, patients receiving volumes greater than 0.3-0.4 ml injected into nodules also experience more pain.

Example 4

Clinical Trial B

In this example, 138 patients with early progressive Dupuytren's disease with a distinct visible/palpable nodule are randomized 1:1 to receive either 40 mg of adalimumab in 0.4 ml total solution or a placebo (0.4 ml of saline). The adalimumab or saline solution is injected directly into the nodule (as discussed in Example 3) at 3 month intervals over 12 months. Patients are then followed for an additional 6 months. Nodule hardness and size is assessed using tonometry and ultrasound ultrasound scans respectively, and disease progression is monitored. Health economic analysis assesses whether adalimumab injections are a cost effective means for preventing the progression of early stage Dupuytren's disease.

Results:

Patients treated with adalimumab as described in this example show improved nodule hardness and size. Additionally, treatment with adalimumab as described in this example slows disease progression compared to patients treated with placebo. Treatment with adalimumab as described in this example is a cost effective means for preventing the progression of early stage Dupuytren's disease.

REFERENCES CITED

Hindocha, S., McGrouther, D. A. & Bavat, A. Epidemiological evaluation of Dupuytren's disease incidence and prevalence rates in relation to etiology. Hand (New York, N.Y.) 4, 256-269 (2009).

Bebbington, E. & Furniss, D. Linear regression analysis of Hospital Episode Statistics predicts a large increase in demand for elective hand surgery in England. Journal of plastic, reconstructive & aesthetic surgery: JPRAS 68, 243-251 (2015).

Lanting, R., van den Heuvel, Westerink, B. & Werker, P. M. Prevalence of Dupuytren disease in The Netherlands. Plastic and reconstructive surgery 132, 394-403 (2013).

Ball C, Pratt A, Nanchahal J (2013). Optimal functional outcome measures for assessing treatment for Dupuytren's Disease: a systematic review and recommendations for future practice. BMC Musculoskeletal Disorders 14(1): 131.

Ball, C., Izadi, D., Verjee, L. S., Chan, J. & Nanchahal, J. Systematic review of non-surgical treatments for early dupuytren's disease. BMC musculoskeletal disorders 17, 345 (2016).

Zhao, J. Z., Hadley, S., Floyd, E., Earp, B. F. & Blazar, P. E. The Impact of Collagenase *Clostridium histolyticum* Introduction on Dupuytren Treatment Patterns in the United States. The Journal of hand surgery 41, 963-968 (2016).

Chen, N. C., Shauver, M. J. & Chung, K. C. Cost-effectiveness of open partial fasciectomy, needle aponeurotomy, and collagenase injection for dupuytren contracture. The Journal of hand surgery 36, 1826-1034 e1832 (2011).

van Rijssen, A. L., ter Linden, H. & Werker, P. M. Five-year results of a randomized clinical trial on treatment in Dupuytren's disease: percutaneous needle fasciotomy versus limited fasciectomy. Plastic and reconstructive surgery 129, 469-477 (2012).

Peimer, C. A., et al. Dupuytren contracture recurrence following treatment with collagenase *Clostridium histolyticum* (CORDLESS study): 3-year data. The Journal of hand surgery 38, 12-22 (2013).

Darby, I. A., Zakuan, N., Billet, F. & Desmouliere, A. The myofibroblast, a key cell in normal and pathological tissue repair. Cell Mol Life Sci 73, 1145-1157 (2016).

Dolmans, G. H., et al. Wnt signaling and Dupuytren's disease. The New England journal of medicine 365, 307-317 (2011).

Bayat, A. & McGrouther, D. A. Management of Dupuytren's disease—clear advice for an elusive condition. Annals of the Royal College of Surgeons of England 88, 3-8 (2006).

Chiu, H. F. & McFarlane, R. M. Pathogenesis of Dupuytren's contracture: a correlative clinical-pathological study. The Journal of hand surgery 3, 1-10 (1978).

Gross J, Lapiere C (1962). "Collagenolytic Activity in Amphibian Tissues: A Tissue Culture Assay". *Proc Natl Acad Sci USA* 48 (6): 1014-22.

Hurst et al. "Injectable Collagenase *Clostridium Histolyticum* for Dupuytren's Contracture" N ENGL J MED 361;10 Sep. 3, 2009.

Kontermann, Roland E. "Dual targeting strategies with bispecific antibodies" mAbs 4:2, 182-197; March/April 2012.

Lam, W. L., Rawlins, J. M., Karoo, R. O., Naylor, I. & Sharpe, D. T. Re-visiting Luck's classification: a histological analysis of Dupuytren's disease. The Journal of hand surgery, European volume 35, 312-317 (2010).

Laursen et al. Pain perception after subcutaneous injections of media containing different buffers. Basic and Clinical Pharmacology and Toxicology 2006, 98: 218-221.

Luck, J. V. Dupuytren's contracture; a new concept of the pathogenesis correlated with surgical management. The Journal of bone and joint surgery. American volume 41-A, 635-664 (1959).

Paladini et al. "Mutations in the Catalytic Domain of Human Matrix Metalloproteinase-1 (MMP-1) That Allow for Regulated Activity through the Use of Ca2+" THE Rombouts, J. J., Noel, H., Legrain, Y. & Munting, E. Prediction of recurrence in the treatment of Dupuytren's disease: evaluation of a histologic classification. The Journal of hand surgery 14, 644-652 (1989).

Rombouts, J Hand Sure Am, 14, 644-652, 1989.

Skalli, O., et al. A monoclonal antibody against alpha-smooth muscle actin: a new probe for smooth muscle differentiation. The Journal of cell biology 103, 2787-2796 (1986).

Summary basis of approval XIAFLEX-EU: Available at www.ema.europa.eu/docs/en_GB/document_library/EPAR_-_Product_Information/human/002048/WC500103373.pdf Tracy et al. "Tumor necrosis factor antagonist mechanisms of action: A comprehensive review" Pharmacology & Therapeutics 117 (2008) 244-279.

VandeBerg, J. S., Rudolph, R., Gelberman, R. & Woodward, M. R. Ultrastructural relationship of skin to nodule and cord in Dupuytren's contracture. Plastic and reconstructive surgery 69, 835-844 (1982).

Verhoekx, J. S., et al. Isometric Contraction of Dupuytren's Myofibroblasts Is Inhibited by Blocking Intercellular Junctions. The Journal of investigative dermatology (2013).

Verjee, L. S., et al. Myofibroblast distribution in Dupuytren's cords: correlation with digital contracture. The Journal of hand surgery 34, 1785-1794 (2009).

Verjee, L. S., et al. Unraveling the signaling pathways promoting fibrosis in Dupuytren's disease reveals TNF as a therapeutic target. Proceedings of the National Academy of Sciences of the United States of America vol. 110 no. 10 published Feb. 19, 2013.

The invention claimed is:

1. A pre-filled syringe for use in treating an individual afflicted with early stage Dupuytren's disease characterized by the presence of a Dupuytren's disease nodule on the individual's hand by injection directly into the Dupuytren's Disease nodule, wherein the syringe comprises:
   a) a pharmaceutical composition in the form of a liquid having a volume between 0.4 ml which is free of citrate and comprises 40 mg of adalimumab, and
   b) a needle on the syringe, the size of which needle is equal to 25 gauge.

2. A pre-filled syringe for use in treating an individual afflicted with early stage Dupuytren's disease characterized by the presence of a Dupuytren's disease nodule on the individual's hand by injection directly into the Dupuytren's Disease nodule, wherein the syringe comprises:
   a) a pharmaceutical composition in the form of a liquid having a volume between 0.4 ml which is free of citrate and comprises 40 mg of adalimumab, and
   b) a needle on the syringe, the size of which needle is equal to 25 gauge, and
      wherein injection of the pharmaceutical composition directly into the nodule results in reduced pain.

* * * * *